United States Patent
Fujiwara et al.

(10) Patent No.: US 8,524,055 B2
(45) Date of Patent: *Sep. 3, 2013

(54) METHOD FOR MEASURING BLOOD COMPONENTS AND BIOSENSOR AND MEASURING INSTRUMENT FOR USE THEREIN

(75) Inventors: Masaki Fujiwara, Ehime (JP); Teppei Shinno, Ehime (JP); Shin Ikeda, Osaka (JP)

(73) Assignee: Panasonic Corporation, Osaka (JP)

( * ) Notice: Subject to any disclaimer, the term of this patent is extended or adjusted under 35 U.S.C. 154(b) by 224 days.

This patent is subject to a terminal disclaimer.

(21) Appl. No.: 13/094,356

(22) Filed: Apr. 26, 2011

(65) Prior Publication Data
US 2011/0198223 A1   Aug. 18, 2011

Related U.S. Application Data

(63) Continuation of application No. 10/598,001, filed as application No. PCT/JP2005/007404 on Apr. 18, 2005, now Pat. No. 7,955,492.

(30) Foreign Application Priority Data

Apr. 19, 2004  (JP) .................................. 2004-123220

(51) Int. Cl.
G01N 27/327 (2006.01)
G01N 33/66 (2006.01)

(52) U.S. Cl.
USPC .................. 204/403.11; 422/68.1; 422/82.01; 435/287.1

(58) Field of Classification Search
USPC .................... 204/403.01–403.15; 422/82.01; 205/792, 777.5, 778; 600/345–348; 435/287.1
See application file for complete search history.

(56) References Cited

U.S. PATENT DOCUMENTS 3,922,598 A  11/1975  Steuer et al.
4,835,477 A   5/1989  Polaschegg et al.
(Continued)

FOREIGN PATENT DOCUMENTS
EP  0 417 796  3/1991
EP  0 537 761  4/1993
(Continued)

OTHER PUBLICATIONS

Varlan, et al., "New design technique for planar conductometric haematocrit sensors", Sensors and Actuators B, vol. 34, No. 1, 258-264, 1996.

*Primary Examiner* — J. Christopher Ball
*Assistant Examiner* — Jennifer Dieterle
(74) *Attorney, Agent, or Firm* — Hamre, Schumann, Mueller & Larson, P.C.

(57) ABSTRACT

The present invention provides a method of measuring a component in blood, by which the amounts of blood cells and an interfering substance can be measured with high accuracy and high reliability and the amount of the component can be corrected accurately based on the amounts of the blood cells and the interfering substance. In a sensor for measuring a blood component, a first working electrode 13 measures a current that flows during a redox reaction of a blood component, a second working electrode 17 measures the amount of blood cells, and a third working electrode 12 measures the amount of an interfering substance. Next, based on the measurement results, the amount of the blood component to be measured is corrected. Thus, more accurate and precise measurement of the amount of the blood component can be realized.

10 Claims, 12 Drawing Sheets

(56) References Cited

U.S. PATENT DOCUMENTS

| | | | |
|---|---|---|---|
| 4,897,162 A | 1/1990 | Lewandowski et al. | |
| 5,264,103 A | 11/1993 | Yoshioka et al. | |
| 5,385,846 A | 1/1995 | Kuhn et al. | |
| 5,463,435 A | 10/1995 | Ezawa | |
| 5,475,454 A | 12/1995 | Ezawa | |
| 5,582,697 A | 12/1996 | Ikeda et al. | |
| 6,287,451 B1 | 9/2001 | Winarta et al. | |
| 6,340,428 B1 | 1/2002 | Ikeda et al. | |
| 6,471,839 B1 | 10/2002 | Yamamoto et al. | |
| 6,541,216 B1 | 4/2003 | Wilsey et al. | |
| 6,599,407 B2* | 7/2003 | Taniike et al. | 204/403.1 |
| 6,632,349 B1 | 10/2003 | Hodges et al. | |
| 6,875,327 B1 | 4/2005 | Miyazaki et al. | |
| 7,018,843 B2 | 3/2006 | Heller | |
| 7,338,639 B2 | 3/2008 | Burke et al. | |
| 2001/0006149 A1 | 7/2001 | Taniike et al. | |
| 2001/0050227 A1 | 12/2001 | Yamamoto et al. | |
| 2002/0048532 A1 | 4/2002 | Lin et al. | |
| 2002/0053523 A1 | 5/2002 | Liamos et al. | |
| 2002/0179442 A1 | 12/2002 | Miyazaki et al. | |
| 2003/0042150 A1 | 3/2003 | Ryu et al. | |
| 2003/0082076 A1 | 5/2003 | Lin et al. | |
| 2003/0098234 A1 | 5/2003 | Hasegawa et al. | |
| 2003/0159945 A1 | 8/2003 | Miyazaki et al. | |
| 2004/0005721 A1 | 1/2004 | Tanike et al. | |
| 2004/0040866 A1 | 3/2004 | Miyashita et al. | |
| 2004/0043477 A1 | 3/2004 | Schibli | |
| 2004/0069628 A1 | 4/2004 | Watanabe et al. | |
| 2004/0079652 A1 | 4/2004 | Vreeke et al. | |
| 2004/0134779 A1 | 7/2004 | Hsu et al. | |
| 2004/0173458 A1 | 9/2004 | Noda et al. | |
| 2004/0232009 A1 | 11/2004 | Okuda et al. | |
| 2005/0023137 A1* | 2/2005 | Bhullar et al. | 204/403.1 |
| 2005/0023152 A1 | 2/2005 | Surridge et al. | |
| 2005/0145490 A1 | 7/2005 | Shinno et al. | |
| 2005/0164328 A1 | 7/2005 | Kuwabata et al. | |
| 2006/0224658 A1 | 10/2006 | Sato et al. | |
| 2007/0062822 A1 | 3/2007 | Fujiwara et al. | |
| 2007/0080073 A1 | 4/2007 | Wu et al. | |
| 2007/0131565 A1 | 6/2007 | Fujiwara et al. | |
| 2010/0270177 A1 | 10/2010 | Fujiwara | |
| 2012/0037506 A1 | 2/2012 | Fujiwara et al. | |

FOREIGN PATENT DOCUMENTS

| | | |
|---|---|---|
| EP | 0 732 406 | 9/1996 |
| EP | 0 735 363 | 10/1996 |
| EP | 0 928 967 | 7/1999 |
| EP | 0 984 069 | 3/2000 |
| EP | 1 152 239 | 11/2001 |
| EP | 1 167 538 | 1/2002 |
| EP | 1 256 798 | 11/2002 |
| EP | 1 411 348 | 4/2004 |
| EP | 1 443 322 | 8/2004 |
| JP | 3-99254 | 4/1991 |
| JP | H11-194108 | 7/1997 |
| JP | 11-118794 | 4/1999 |
| JP | 2000-039416 | 2/2000 |
| JP | 2000-065778 | 3/2000 |
| JP | 2001-91512 | 4/2001 |
| JP | 2001-091512 | 4/2001 |
| JP | 2001-201479 | 7/2001 |
| JP | 2001-527215 | 12/2001 |
| JP | 2002/057767 | 1/2002 |
| JP | 3267933 | 1/2002 |
| JP | 2003-501627 | 1/2003 |
| JP | 3369183 | 1/2003 |
| JP | 2003-521708 | 7/2003 |
| JP | 2004-117342 | 4/2004 |
| JP | 2004-163411 | 6/2004 |
| JP | 2005-114359 | 4/2005 |
| JP | 2005-147990 | 6/2005 |
| WO | 94/29731 | 12/1994 |
| WO | 96/32883 | 10/1996 |
| WO | 97/16726 | 5/1997 |
| WO | 99/32881 | 7/1999 |
| WO | 00/73785 | 12/2000 |
| WO | 01/57510 | 8/2001 |
| WO | 03/008956 | 1/2003 |
| WO | 03/034055 | 4/2003 |
| WO | 03/089658 | 10/2003 |
| WO | 2004/011921 | 2/2004 |
| WO | 2005/040407 | 5/2005 |

\* cited by examiner

METHOD FOR MEASURING BLOOD COMPONENTS AND BIOSENSOR AND MEASURING INSTRUMENT FOR USE THEREIN

CROSS-REFERENCE TO RELATED APPLICATIONS

This application is a Continuation of application Ser. No. 10/598,001, filed Aug. 15, 2006, which is a U.S. National Stage of PCT/JP2005/007404, filed Apr. 18, 2005, which applications are incorporated herein by reference.

TECHNICAL FIELD

The present invention relates to a method of measuring a blood component and to a biosensor and a measuring device used in the method.

BACKGROUND ART

Conventionally, sensors for measuring a blood component have been used for clinical tests, self-measurement of blood glucose level by diabetics, etc. The configuration of the sensor for measuring a blood component is such that, for example, a cover is disposed on an insulating substrate having a working electrode and a counter electrode on its surface with a spacer intervening between the cover and the insulating substrate. On the working electrode and the counter electrode, a reagent containing an oxidoreductase, a mediator (an electron carrier), and the like is provided, thereby forming an analysis portion. The analysis portion communicates with one end of a channel for leading blood to the analysis portion. The other end of the channel is open toward the outside of the sensor so as to serve as a blood supply port. Blood component analysis (e.g., analysis of blood glucose level) using the sensor configured as above is carried out in the following manner, for example. First, the sensor is set in a dedicated measuring device (a meter). Then, a fingertip or the like is punctured with a lancet to cause bleeding, and the blood supply port of the sensor is brought into contact with the blood that has come out. The blood is drawn into the channel of the sensor by capillary action and flows through the channel to be led to the analysis portion where the blood comes into contact with the reagent. Then, a redox reaction occurs between a component in the blood and the oxidoreductase so that electrons move to the electrodes via the mediator. A current caused to flow at this time is detected, and the measuring device converts the detected current into the amount of the blood component and displays the value obtained by the conversion.

However, the sensor response of an electrochemical blood glucose sensor as described above may be affected by an interfering substance such as an easily oxidizable compound (e.g., ascorbic acid or uric acid) and the amount of blood cells/hematocrit (Hct). Thus, in order to obtain an accurate measured value, it is necessary to quantitate the interfering substance, the blood cells, or both the interfering substance and the blood cells and then correct the amount of the blood component (e.g., the blood glucose level) based on the value (s) obtained by the quantitation. For example, there has been a sensor that corrects the amount of a blood component by measuring the amount of blood cells by the use of two working electrodes and one reference electrode (see Patent Document 1). Other than this, there has been a method in which the amount of blood cells is measured using a mediator (see Patent Document 2). Also, there has been a method in which an interfering substance is quantitated using an interfering substance-detecting electrode (see Patent Document 3). However, the conventional techniques have a problem concerning the accuracy and the reliability of the measured amounts of the blood cells and the interfering substance so that the amount of the blood component cannot be corrected sufficiently.

[Patent Document 1] JP 2003-501627 A
[Patent Document 2] Japanese Patent No. 3369183
[Patent Document 3] Japanese Patent No. 3267933

DISCLOSURE OF INVENTION

Problem to be Solved by the Invention

With the foregoing in mind, it is an object of the present invention to provide a method of measuring a blood component, by which the amount of a blood component can be corrected accurately by measuring the amount of blood cells and the amount of an interfering substance with high accuracy and high reliability and also to provide a sensor and a measuring device used in the method.

Means for Solving Problem

In order to achieve the above object, the present invention provides a method of measuring a component in blood, including the steps of: measuring a component in blood by causing a redox reaction between the component and an oxidoreductase in the presence of a mediator, detecting a redox current caused by the redox reaction with a first electrode system including a working electrode and a counter electrode, and converting a value of the detected current into an amount of the component; correcting the amount of the component using an amount of blood cells contained in the blood; and correcting the amount of the component using an amount of an interfering substance contained in the blood. The correction step using the amount of the blood cells includes: providing a second electrode system including a working electrode and a counter electrode; providing a mediator on the counter electrode of the second electrode system but not on the working electrode of the second electrode system; supplying the blood to the second electrode system; applying a voltage to the second electrode system in this state to cause a redox current to flow through the second electrode system; detecting the redox current; converting a value of the detected redox current into the amount of the blood cells; and correcting the amount of the component based on the amount of the blood cells. The correction step using the amount of the interfering substance includes: providing a third electrode system including a working electrode and a counter electrode; supplying the blood to the third electrode system; applying a voltage to the third electrode system in this state to cause a redox current to flow through the third electrode system; detecting the redox current; converting a value of the detected redox current into the amount of the interfering substance; and correcting the amount of the component based on the amount of the interfering substance.

Furthermore, the present invention provides a biosensor for measuring a component in blood by causing a redox reaction of the component and detecting a redox current caused by the redox reaction with an electrode. The biosensor includes: a first analysis portion including a first electrode system on which at least an oxidoreductase that acts upon the component and a mediator are provided; a second analysis portion including a second electrode system that includes a working electrode and a counter electrode, a mediator being provided on the counter electrode but not on the working electrode; and a third analysis portion including a third electrode system that includes a working electrode and a counter electrode. In the first analysis portion, the component in the blood is measured by causing a redox reaction between the component and the oxidoreductase in the presence of the mediator and detecting with the first electrode system a redox current caused to flow when a voltage is applied. In the second analysis portion, an amount of blood cells contained in the blood is measured by supplying the blood to the second electrode system, applying a voltage to the second electrode system in this state to cause a redox current to flow through the second electrode system, and detecting the redox current. In the third analysis portion, an amount of an interfering substance contained in the blood is measured by supplying the blood to the third electrode system, applying a voltage to the third electrode system in this state to cause a current to flow through the third electrode system, and detecting the current.

Still further, the present invention provides a measuring device for measuring a component in blood using the above-described biosensor. The measuring device includes: measurement means for measuring a component in blood by causing a redox reaction between the component and the oxidoreductase, detecting a redox current caused by the redox reaction with the first electrode system, and converting the detected current into an amount of the component; correction means for correcting the amount of the component using an amount of blood cells contained in the blood; and correction means for correcting the amount of the component using an amount of an interfering substance contained in the blood. The correction means using the amount of the blood cells uses the second electrode system for measuring the amount of the blood cells and carries out the correction by applying a voltage to the second electrode system in the presence of the blood to cause a current to flow, detecting the current, converting a value of the detected current into the amount of the blood cells, and correcting the amount of the component based on the amount of the blood cells. The correction means using the amount of the interfering substance uses the third electrode system for measuring the amount of the interfering substance and carries out the correction by applying a voltage to the third electrode system in the presence of the blood to cause a current to flow, detecting the current, converting a value of the detected current into the amount of the interfering substance, and correcting the amount of the components based on the amount of the interfering substance.

Effects of the Invention

As described above, in the measurement of a blood component, the amount of blood cells and the amount of an interfering substance can be measured with high accuracy by providing a plurality of working electrodes and measuring the amount of the blood component using one of the working electrodes and the amount of the blood cells and the amount of the interfering substance using the other working electrodes. As a result, the correction of the amount of the blood component using the amounts of the blood cells and the interfering substance can be performed with high accuracy and high reliability.

BRIEF DESCRIPTION OF DRAWINGS

FIG. 13 is a graph showing an example of the result of measurement of a response current for determining the amount of blood cells.
FIG. 14 is a graph showing another example of the result of measurement of a response current for determining the amount of blood cells.
FIG. 15 is a graph showing still another example of the result of measurement of a response current for determining the amount of blood cells.
FIG. 16 is a graph showing still another example of the result of measurement of a response current for determining the amount of blood cells.
FIG. 17 is a graph showing still another example of the result of measurement of a response current for determining the amount of blood cells.

Figure 1:
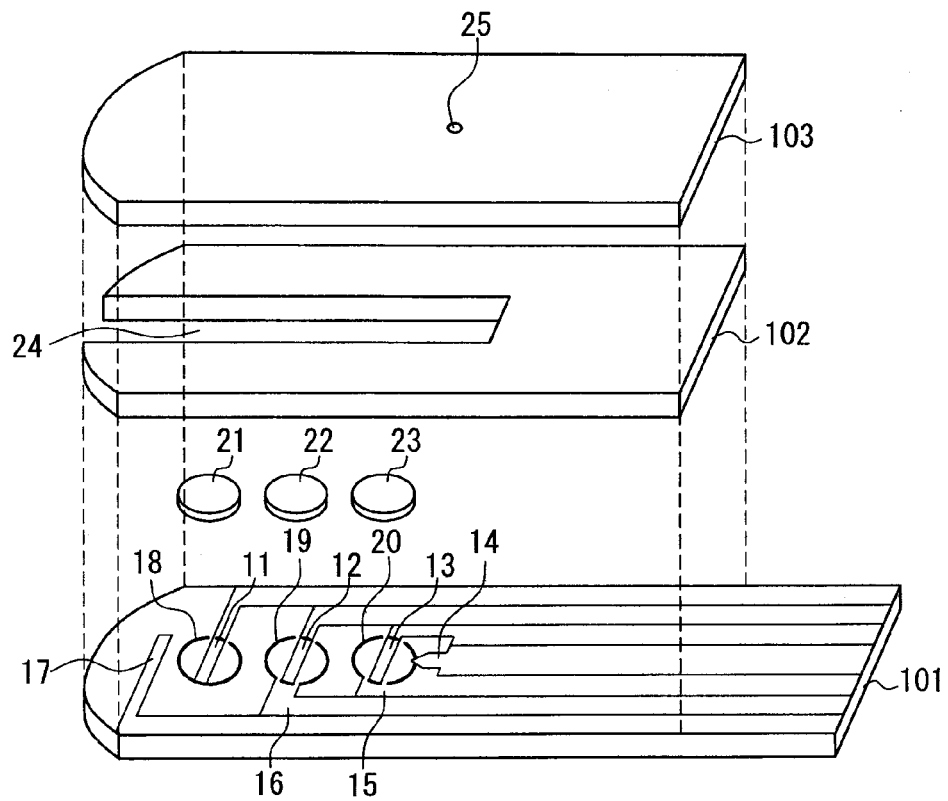
FIG. 1 is an exploded perspective view showing an example of a sensor according to the present invention.

EXPLANATION OF REFERENCE NUMERALS 11 second counter electrode
12, 32, 52 third working electrode
13, 33, 53 first working electrode
14, 34, 54 liquid detecting electrode
15, 35, 55 first counter electrode
16, 36 third counter electrode
17, 37, 57 second working electrode
18, 19, 20, 39, 40, 60 round slit portion
21 second reagent layer
22, 42 third reagent layer
23, 43, 63 first reagent layer
24, 44, 64 channel
25, 45, 65 air hole 101, 301, 501 insulating substrate
102, 302, 502 spacer
103, 303, 503 cover

DESCRIPTION OF THE INVENTION

In the present invention, the correction based on the amount of the blood cells preferably is carried out using at least one of a calibration curve and a calibration table that have been prepared previously for showing the relationship between an amount of the blood cells and an amount of the blood component. Furthermore, in the present invention, the correction based on the amount of the interfering substance preferably is carried out using at least one of a calibration curve and a calibration table that have been prepared previously for showing the relationship between an amount of the interfering substance and an amount of the blood component.

In the present invention, it is preferable that, in the third electrode system, a mediator is provided at least on the counter electrode.

In the present invention, at least one electrode selected from the working electrodes and the counter electrodes of the first electrode system, the second electrode system, and the third electrode system may serve also as any of the other electrodes. In the method of measuring a blood component according to the present invention, an electrode that is used as a working electrode in a certain step may be used as a counter electrode in another step, and vice versa.

In the present invention, the order of measuring the amount of the blood component, the amount of the blood cells, and the amount of the interfering substance is not particularly limited, but it is preferable that the amount of the blood cells is measured last. Either of the amount of the blood component or the amount of the interfering substance may be measured first, or they may be measured at the same time.

In the present invention, it is preferable that a voltage for pretreating the third electrode system is applied to the third electrode system before measuring the amount of the interfering substance. By this pretreatment, the surface of the third electrode system is cleaned, so that the amount of the interfering substance and the amount of the blood cells can be measured more accurately.

In the present invention, the voltage applied to the working electrode of the third electrode system to perform the pretreatment preferably is in the range from 0.01 to 1 V relative to the counter electrode of the third electrode system.

In the present invention, the voltage applied to the working electrode of the third electrode system to measure the amount of the interfering substance preferably is in the range from 0.01 to 1 V and more preferably in the range from 0.01 to 0.5 V relative to the counter electrode of the third electrode system.

In the present invention, the voltage applied to the working electrode of the second electrode system to measure the amount of the blood cells preferably is at least 1 V, more preferably in the range from 1 to 10 V, and still more preferably in the range from 1 to 5 V relative to the counter electrode of the second electrode system.

In the present invention, the blood component to be measured is, for example, glucose, lactic acid, uric acid, bilirubin, cholesterol, or the like. Furthermore, the oxidoreductase is selected as appropriate depending on the blood component to be measured. Examples of the oxidoreductase include glucose oxidase, lactate oxidase, cholesterol oxidase, bilirubin oxidase, glucose dehydrogenase, and lactate dehydrogenase. The amount of the oxidoreductase is, for example, 0.01 to 100 U, preferably 0.05 to 10 U, and more preferably 0.1 to 5 U per one sensor or one measurement. When the blood component to be measured is glucose, the oxidoreductase to be used preferably is glucose oxidase or glucose dehydrogenase.

Preferably, the biosensor according to the present invention is configured so that it further includes a channel for leading blood to the biosensor, and the working electrode of the second analysis portion or the third analysis portion is located furthest upstream and the remaining electrodes are located downstream with respect to flow of the blood supplied from one end of the channel.

In the biosensor according to the present invention, it is preferable that the first analysis portion is located furthest downstream in the channel.

In the biosensor according to the present invention, it is not always necessary to provide a mediator on the working electrode of the third electrode system. When the mediator is not provided on the working electrode of the third electrode system, the second electrode system and the third electrode system may share the same working electrode. Also, in this case, either one or a combination of the electrodes of the first electrode system may be shared with at least one of the second electrode system and the third electrode system as the counter electrode.

In the biosensor according to the present invention, the second electrode system and the third electrode system may share an electrode, which is used as the counter electrode in the second electrode system and as the working electrode in the third electrode system.

In the biosensor according to the present invention, the mediator may be provided on the working electrode of the third electrode system, and in this case, the second electrode system and the third electrode system may share an electrode, which is used as the working electrode in the third electrode system and as the counter electrode in the second electrode system, and the third electrode system and the first electrode system may share the same counter electrode.

Preferably, the biosensor according to the present invention is configured so that it further includes a liquid detecting electrode, and the liquid detecting electrode is located downstream from at least one of the analysis portions so that whether or not the blood is supplied to the at least one of the analysis portions can be detected with the liquid detecting electrode. The liquid detecting electrode can prevent the occurrence of measurement error due to the lack of blood supplied to the biosensor, so that more accurate measurement of the amount of the blood component becomes possible. Note here that at least one of the working electrodes and the counter electrodes of the first electrode system, the second electrode system, and the third electrode system may serve also as the liquid detecting electrode. Furthermore, it is preferable that the measuring device according to the present invention further includes detection means that detects whether or not the blood is supplied inside the biosensor with the liquid detecting electrode.

In the present invention, a mediator may be used. There is no particular limitation regarding the mediator to be used. Examples of the mediator include ferricyanides, p-benzoquinone, p-benzoquinone derivatives, phenazine methosulfate, methylene blue, ferrocene, and ferrocene derivatives. Among these, ferricyanides are preferable, and potassium ferricyanide is more preferable. The amount of the mediator to be blended is not particularly limited, but is, for example, 0.1 to 1000 mM, preferably 1 to 500 mM, and more preferably 10 to 200 mM per one measurement or one sensor.

In the present invention, each of the electrodes preferably is coated with a polymeric material in order to prevent adhesion of impurities, oxidation of the electrode, and the like.

Examples of the polymeric material include carboxymethyl cellulose (CMC), hydroxyethyl cellulose, hydroxypropyl cellulose, methyl cellulose, ethyl cellulose, ethyl hydroxyethyl cellulose, carboxyethyl cellulose, polyvinyl alcohol, polyvinylpyrrolidone, polyamino acid such as polylysine, polystyrene sulfonate, gelatin and derivatives thereof, polyacrylic acid and salts thereof, polymethacrylic acid and salts thereof, starch and derivatives thereof, maleic anhydride polymer and salts thereof, and agarose gel and derivatives thereof. They may be used individually or two or more of them may be used together. The method of coating the electrode with a polymeric material is not particularly limited. For example, the coating can be achieved by providing a polymeric material solution, applying the solution to the electrode surface, and then removing a solvent contained in the coating layer of the solution by drying.

Hereinafter, examples of a sensor for measuring a blood component and the like according to the present invention will be described with reference to the drawings.

Example 1

Figure 2:
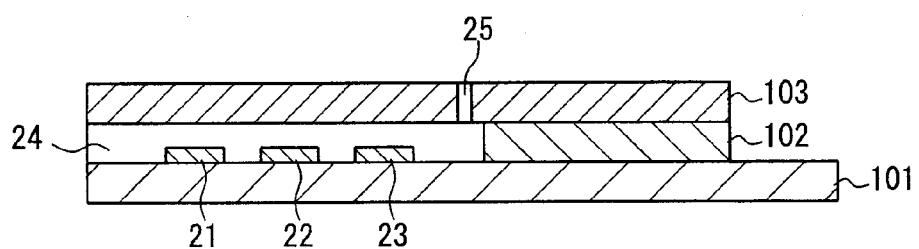
FIG. 2 is a sectional view of the sensor shown in FIG. 1.
Figure 3:
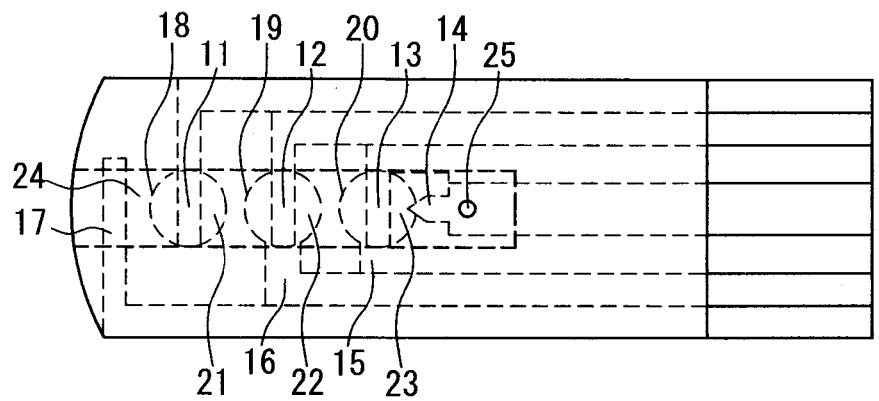
FIG. 3 is a plan view of the sensor shown in FIG. 1.

FIGS. 1, 2, and 3 show one example of a sensor for measuring a blood component according to the present invention. FIG. 1 is an exploded perspective view of the sensor, FIG. 2 is a sectional view of the sensor, and FIG. 3 is a plan view of the sensor. In these three drawings, the same components are given the same reference numerals.

As shown in the drawings, in this sensor, a first electrode system including a first working electrode 13 and a first counter electrode 15, a second electrode system including a second working electrode 17 and a second counter electrode 11, a third electrode system including a third working electrode 12 and a third counter electrode 16, and a liquid detecting electrode 14 are formed on an insulating substrate 101. A first reagent layer 23 is provided on the first electrode system, a second reagent layer 21 is provided on the second counter electrode 11, and a third reagent layer 22 is provided on the third electrode system. The first reagent layer 23 contains an oxidoreductase such as glucose dehydrogenase and a mediator such as potassium ferricyanide and optionally contains an enzyme stabilizer, a crystal homogenizing agent, and the like. Each of the second reagent layer 21 and the third reagent layer 22 contains a mediator such as potassium ferricyanide and optionally contains an enzyme stabilizer, a crystal homogenizing agent, and the like. A cover 103 is disposed on the insulating substrate 101 so as to cover an entire area excluding one end portion (the end portion on the right in the drawings) with a spacer 102 intervening therebetween. In this sensor, the insulating substrate 101, the spacer 102, and the cover 103 form a channel 24 for leading blood to the respective electrodes (11 to 17). The channel 24 extends to the other end portion (the end portion on the left in the drawings) of the sensor, and the tip of the channel 24 is open toward the outside of the sensor so as to serve as a blood supply port. The seven electrodes (11 to 17) are connected to leads, respectively. These leads extend to the above-described one end portion (the end portion on the right in the drawings) of the sensor with the tip of each lead not being covered with the cover but being exposed. The cover 103 has an air hole 25 at a portion corresponding to the right end portion of the channel 24.

In the present invention, the material of the insulating substrate is not particularly limited, and may be, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), a methacrylic resin (PMMA), an ABS resin (ABS), or glass. Among these, polyethylene terephthalate (PET), polycarbonate (PC), and polyimide (PI) are preferable, and polyethylene terephthalate (PET) is more preferable. The size of the insulating substrate is not particularly limited. For example, the insulating substrate may have an overall length of 5 to 100 mm, a width of 2 to 50 mm, and a thickness of 0.05 to 2 mm; preferably an overall length of 7 to 50 mm, a width of 3 to 20 mm, and a thickness of 0.1 to 1 mm; and more preferably an overall length of 10 to 30 mm, a width of 3 to 10 mm, and a thickness of 0.1 to 0.6 mm. Note here that the above description as to the material and the size of the insulating substrate also applies to Examples 2 to 6 to be described later.

The electrodes and the leads on the insulating substrate may be formed by, for example, forming a conductive layer with gold, platinum, palladium, or the like by sputtering or vapor deposition and then processing the conductive layer into a particular electrode pattern with a laser. Examples of the laser include YAG lasers, $CO_2$ lasers, and excimer lasers. Note here that this also applies to Examples 2 to 6 to be described later.

The first reagent layer 23 is formed in the following manner. For example, an aqueous solution containing 0.1 to 5 U/sensor of glucose dehydrogenase, 10 to 200 mM of potassium ferricyanide, 1 to 50 mM of maltitol, and 20 to 200 mM of taurine is dropped on a round slit portion 20 and then is dried. By providing this slit portion 20, it becomes possible to suppress the spreading of the droplet of the aqueous solution, thereby allowing the first reagent layer 23 to be provided at a desired position more accurately. In this manner, the first reagent layer 23 is formed on the first working electrode 13 and the first counter electrode 15. The drying may be natural drying or forced drying using warm air, for example. However, if the temperature of the warm air is too high, there is a possibility that the enzyme contained in the solution might be deactivated. Thus, the temperature of the warm air preferably is around 50° C.

The second reagent layer 21 is formed in the following manner. For example, an aqueous solution containing 10 to 200 mM of potassium ferricyanide and 20 to 200 mM of taurine is dropped on a round slit portion 18 and then is dried. By providing this slit portion 18, it becomes possible to suppress the spreading of the droplet of the aqueous solution, thereby allowing the second reagent layer 21 to be provided at a desired position more accurately. In this manner, the second reagent layer 21 is formed on the second counter electrode 11.

The third reagent layer 22 is formed in the following manner. For example, an aqueous solution containing 10 to 200 mM of potassium ferricyanide and 20 to 200 mM of taurine is dropped on a round slit portion 19 and then is dried. By providing this slit portion 19, it becomes possible to suppress the spreading of the droplet of the aqueous solution, thereby allowing the third reagent layer 22 to be provided at a desired position more accurately. In this manner, the third reagent layer 22 is formed on the third working electrode 12 and the third counter electrode 16.

In the present invention, the material of the spacer is not particularly limited. For example, the same material as that of the insulating substrate can be used. The size of the spacer also is not particularly limited. For example, the spacer may have an overall length of 5 to 100 mm, a width of 2 to 50 mm, and a thickness of 0.01 to 1 mm; preferably an overall length of 7 to 50 mm, a width of 3 to 20 mm, and a thickness 0.05 to 0.5 mm; and more preferably an overall length of 10 to 30 mm, a width of 3 to 10 mm, and a thickness of 0.05 to 0.25 mm. The spacer has an I-shaped cut-away portion that serves as the channel for leading blood. The cut-away portion may have, for example, an overall length of 0.5 to 8 mm and a width of 0.1 to 5 mm; preferably an overall length of 1 to 10 mm and a width of 0.2 to 3 mm; and more preferably an overall length of 1 to 5 mm and a width of 0.5 to 2 mm. The cut-away portion may be formed, for instance, by using a laser, a drill, or the like, or by forming the spacer using a die that can form the spacer provided with the cut-away portion. Note here that the above description as to the material and the size of the spacer and the cut-away portion also applies to Examples 2 to 6 to be described later.

In the present invention, the material of the cover is not particularly limited. For example, the same material as that of the insulating substrate can be used. It is more preferable that a portion of the cover corresponding to the ceiling of the channel for leading blood to the sensor is subjected to a treatment for imparting hydrophilicity. The treatment for imparting hydrophilicity may be carried out by, for example, applying a surfactant or introducing a hydrophilic functional group such as a hydroxyl group, a carbonyl group, or a carboxyl group to the surface of the cover by plasma processing or the like. Furthermore, a layer formed of a surfactant such as lecithin may be formed on the reagent layer. The size of the cover is not particularly limited. For example, the cover may have an overall length of 5 to 100 mm, a width of 3 to 50 mm, and a thickness of 0.01 to 0.5 mm; preferably an overall length of 10 to 50 mm, a width of 3 to 20 mm, and a thickness of 0.05 to 0.25 mm; and more preferably an overall length of 15 to 30 mm, a width of 5 to 10 mm, and a thickness of 0.05 to 0.1 mm. The cover preferably has an air hole, and the shape of the air hole may be, for example, circular, oval, polygonal, or the like, and the maximum diameter thereof may be, for example, 0.01 to 10 mm, preferably 0.05 to 5 mm, and more preferably 0.1 to 2 mm. The air hole may be formed, for instance, by perforating the cover with a laser, a drill, or the like, or by forming the cover using a die that can form the cover provided with the air hole. Note here that the above description as to the material and the size of the cover and the air hole also applies to Examples 2 to 6 to be described later.

By laminating the insulating substrate, the spacer, and the cover in this order and integrating them, the sensor can be obtained. The integration can be achieved by adhering these three components with an adhesive or through heat-sealing. As the adhesive, an epoxy adhesive, an acrylic adhesive, a polyurethane adhesive, a thermosetting adhesive (a hot melt adhesive or the like), a UV curable adhesive, or the like can be used, for example. Note here that this also applies to Examples 2 to 6 to be described later.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1; Detecting Specimen (Blood))

The supply of blood to the sensor is detected by applying a voltage between the first counter electrode 15 and the liquid detecting electrode 14. It is to be noted here that the combination of the electrodes used for the blood supply detection is by no means limited to the above combination. After the supply of the blood has been confirmed, the subsequent step is started. The voltage applied in Step 1 is, for example, 0.05 to 1.0 V, preferably 0.1 to 0.8 V, and more preferably 0.2 to 0.5 V.

(Step 2: Measuring Glucose)

After allowing glucose in the blood to react with an oxidoreductase for a certain period of time, a voltage is applied to the first working electrode 13. In this step, the first working electrode 13 is used as a working electrode and the first counter electrode 15 is used as a counter electrode. A reduced mediator generated on the first working electrode 13 through the enzyme reaction is oxidized, and the oxidation current caused at this time is detected. The glucose is allowed to react with the oxidoreductase for, for example, 0 to 60 seconds, preferably 1 to 30 seconds, and more preferably 2 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Amount of Interfering Substance)

By applying a voltage to the third working electrode 12, a current caused by the electrolytic oxidation reaction of the interfering substance is detected. In this step, the third working electrode 12 is used as a working electrode and the third counter electrode 16 is used as a counter electrode. The amount of the interfering substance is determined based on the result of this detection. The amount of the interfering substance is used for the correction in the measurement of the glucose. In this correction, the amount of the interfering substance determined using a previously prepared calibration curve showing the relationship between a current and an amount of the interfering substance may be used or alternatively the detected current may be used as it is. In Step 3, the voltage applied is, for example, 0.01 to 1 V and preferably 0.01 to 0.5 V, and the voltage application time is, for example, 0.001 to 60 seconds, preferably 0.01 to 10 seconds, and more preferably 0.01 to 5 seconds. In the present example, both the working electrode and the counter electrode of the third electrode system are provided with the mediator. Accordingly, a current caused by the electrolytic oxidation reaction of the interfering substance is large, so that the amount of the interfering substance can be measured more accurately.

(Step 4: Measuring Amount of Blood Cells)

By applying a voltage to the second working electrode 17, an electrolytic current depending on the amount of the blood cells can be detected. In this step, the second working electrode 17 is used as a working electrode and the second counter electrode 11 is used as a counter electrode. The amount of the blood cells is determined based on the result of this detection. The amount of the blood cells is used for the correction in the measurement of the glucose. In this correction, the amount of the blood cells determined using a previously prepared calibration curve showing the relationship between an electrolytic current and an amount of the blood cells may be used or alternatively the detected electrolytic current may be used as it is. In Step 4, the voltage applied is, for example, 1 to 10 V, preferably 1 to 5 V, and more preferably 2 to 3 V, and the voltage application time is, for example, 0.001 to 60 seconds, preferably 0.01 to 10 seconds, and more preferably 0.01 to 5 seconds.

(Step 5: Correcting Amount of Blood Component)

The amount of the glucose obtained in Step 2 is corrected using the amount of the interfering substance measured in Step 3 and the amount of the blood cells measured in Step 4. Preferably, the correction is carried out based on a calibration curve (including a calibration table) prepared previously. The corrected amount of the glucose is displayed on or stored in the measuring device.

Example 2

Figure 4:
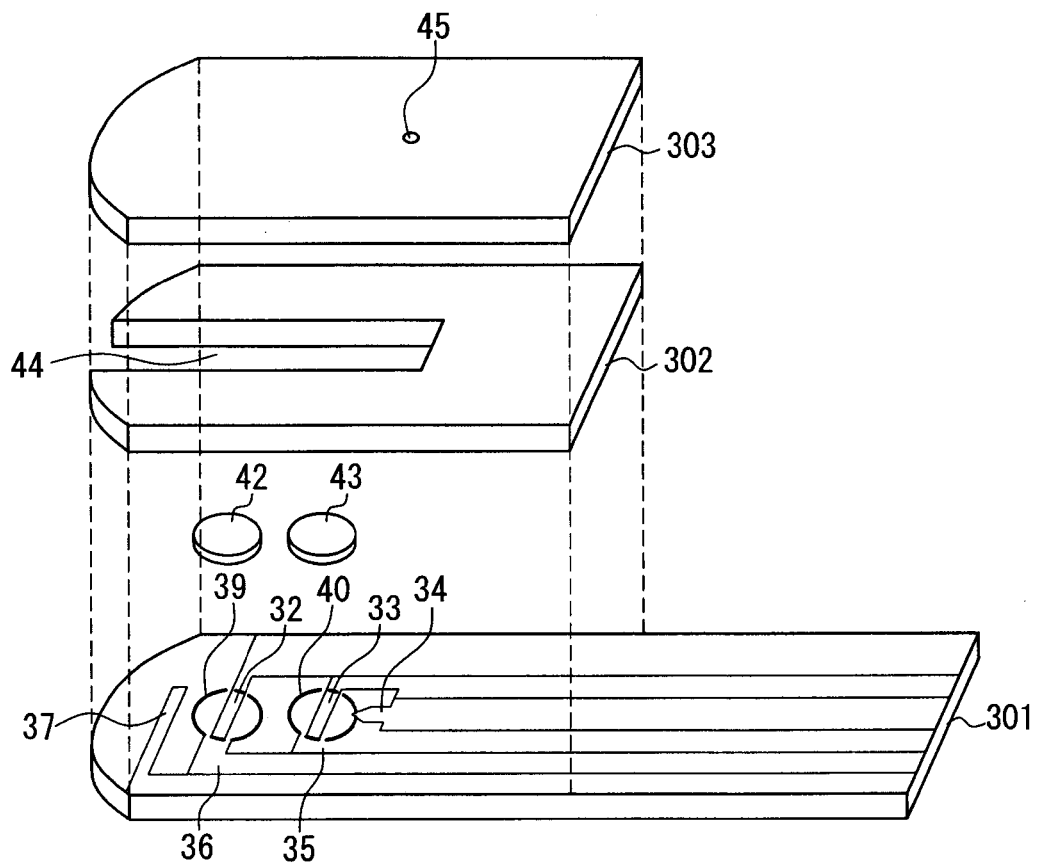
FIG. 4 is an exploded perspective view of another example of a sensor according to the present invention.
Figure 5:
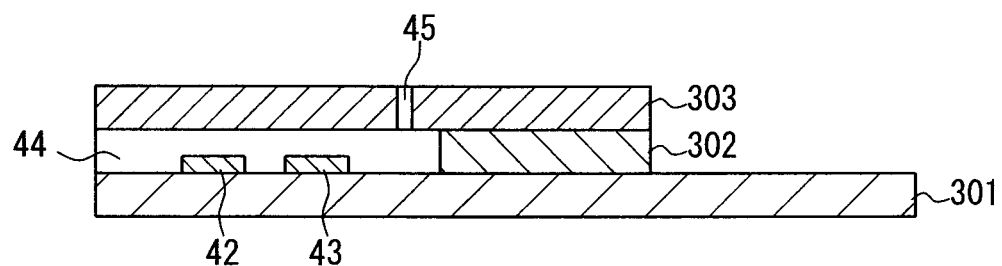
FIG. 5 is a sectional view of the sensor shown in FIG. 4.
Figure 6:
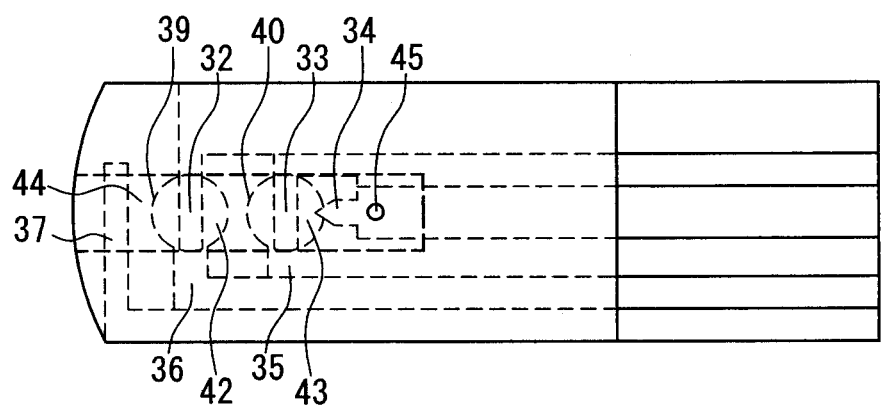
FIG. 6 is a plan view of the sensor shown in FIG. 4.

FIGS. 4, 5, and 6 show another example of a sensor for measuring a blood component according to the present invention. FIG. 4 is an exploded perspective view of the sensor, FIG. 5 is a sectional view of the sensor, and FIG. 6 is a plan view of the sensor. In these three drawings, the same components are given the same reference numerals. In the sensor according to the present example, either one or the combination of the electrodes of the first or third electrode system serves as the counter electrode of the second electrode system of the sensor according to Example 1. Through the shared use of the electrode as described above, it is possible to make the channel for leading blood to the sensor shorter, thereby allowing the amount of blood required as a specimen to be reduced. Moreover, through the shared use of the electrode, the number of the reagent layers can be reduced to two.

As shown in the drawings, in this sensor, a first electrode system including a first working electrode 33 and a first counter electrode 35, a second working electrode 37, a third electrode system including a third working electrode 32 and a third counter electrode 36, and a liquid detecting electrode 34 are formed on an insulating substrate 301. A first reagent layer 43 is provided on the first electrode system, and a third reagent layer 42 is provided on the third electrode system. The first reagent layer 43 contains an oxidoreductase such as glucose dehydrogenase and a mediator such as potassium ferricyanide and optionally contains an enzyme stabilizer, a crystal homogenizing agent, and the like. The third reagent layer 42 contains a mediator such as potassium ferricyanide and optionally contains an enzyme stabilizer, a crystal homogenizing agent, and the like. A cover 303 is disposed on the insulating substrate 301 so as to cover an entire area excluding one end portion (the end portion on the right in the drawings) with a spacer 302 intervening therebetween. In this sensor, the insulating substrate 301, the spacer 302, and the cover 303 form a channel 44 for leading blood to the respective electrodes (32 to 37). The channel 44 extends to the other end portion (the end portion on the left in the drawings) of the sensor, and the tip of the channel 44 is open toward the outside of the sensor so as to serve as a blood supply port. The six electrodes (32 to 37) are connected to leads, respectively. These leads extend to the above-described one end portion (the end portion on the right in the drawings) of the sensor with the tip of each lead not being covered with the cover but being exposed. The cover 303 has an air hole 45 at a portion corresponding to the right end portion of the channel 44.

The first reagent layer 43 is formed in the following manner. For example, an aqueous solution containing 0.1 to 5 U/sensor of glucose dehydrogenase, 10 to 200 mM of potassium ferricyanide, 1 to 50 mM of maltitol, and 20 to 200 mM of taurine is dropped on a round slit portion 40 and then is dried. By providing this slit portion 40, it becomes possible to suppress the spreading of the droplet of the aqueous solution, thereby allowing the first reagent layer 43 to be provided at a desired position more accurately. In this manner, the first reagent layer 43 is formed on the first working electrode 33 and the first counter electrode 35. The drying may be natural drying or forced drying using warm air, for example. However, if the temperature of the warm air is too high, there is a possibility that the enzyme contained in the solution might be deactivated. Thus, the temperature of the warm air preferably is around 50° C.

The third reagent layer 42 is formed in the following manner. For example, an aqueous solution containing 10 to 200 mM of potassium ferricyanide and 20 to 200 mM of taurine is dropped on a round slit portion 39 and then is dried. By providing this slit portion 39, it becomes possible to suppress the spreading of the droplet of the aqueous solution, thereby allowing the third reagent layer 42 to be provided at a desired position more accurately. In this manner, the third reagent layer 42 is formed on the third working electrode 32 and the third counter electrode 36.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1: Detecting Specimen (Blood))

The supply of blood to the sensor is detected by applying a voltage between the first counter electrode 35 and the liquid detecting electrode 34. It is to be noted here that the combination of the electrodes used for the blood supply detection is by no means limited to the above combination. After the supply of the blood has been confirmed, the subsequent step is started. The voltage applied in Step 1 is, for example, 0.05 to 1.0 V, preferably 0.1 to 0.8 V, and more preferably 0.2 to 0.5 V.

(Step 2: Measuring Glucose)

After allowing glucose in the blood to react with an oxidoreductase for a certain period of time, a voltage is applied to the first working electrode 33. In this step, the first working electrode 33 is used as a working electrode and the first counter electrode 35 is used as a counter electrode. A reduced mediator generated on the first working electrode 33 through the enzyme reaction is oxidized, and the oxidation current caused at this time is detected. The glucose is allowed to react with the oxidoreductase for, for example, 0 to 60 seconds, preferably 1 to 30 seconds, and more preferably 2 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Amount of Interfering Substance)

By applying a voltage to the third working electrode 32, a current caused by the electrolytic oxidation reaction of the interfering substance is detected. In this step, the third working electrode 32 is used as a working electrode and the third counter electrode 36 is used as a counter electrode. The amount of the interfering substance is determined based on the result of this detection. The amount of the interfering substance is used for the correction in the measurement of the glucose. In this correction, the amount of the interfering substance determined using a previously prepared calibration curve showing the relationship between a current and an amount of the interfering substance may be used or alternatively the detected current may be used as it is. In Step 3, the voltage applied is, for example, 0.01 to 1 V and preferably 0.01 to 0.5 V, and the voltage application time is, for example, 0.001 to 60 seconds, preferably 0.01 to 10 seconds, and more preferably 0.01 to 5 seconds.

(Step 4: Measuring Amount of Blood Cells)

By applying a voltage to the second working electrode 37, an electrolytic current depending on the amount of the blood cells can be detected. In this step, the second working electrode 37 is used as a working electrode and the third working electrode 32 is used as a counter electrode. The amount of the blood cells is determined based on the result of this detection. The amount of the blood cells is used for the correction in the measurement of the glucose. In this correction, the amount of the blood cells determined using a previously prepared calibration curve showing the relationship between an electrolytic current and an amount of the blood cells may be used or alternatively the detected electrolytic current may be used as it is. In Step 4, the voltage applied is, for example, 1 to 10 V, preferably 1 to 5 V, and more preferably 2 to 3 V, and the voltage application time is, for example, 0.001 to 60 seconds, preferably 0.01 to 10 seconds, and more preferably 0.01 to 5 seconds. Preferably, Step 4 is performed as a last step in the series of steps. Although the third working electrode 32 is used as the counter electrode in the present example, the present invention is not limited thereto. It should be noted that the first working electrode 33 alone, the first counter electrode 35 alone, the third counter electrode 36 alone, the combination of the third working electrode 32 and the third counter electrode 36, or the combination of the first working electrode 33 and the first counter electrode 35 also may be used as the counter electrode.

The reason why the measurement of the amount of the blood cells is performed last is as follows. When the amount of the blood cells is measured before measuring the amount of the blood component and the amount of the interfering substance, the following phenomenon occurs. That is, although the mediator that initially is in an oxidized state (e.g., potassium ferricyanide) is provided on the electrode(s) used as the counter electrode, the mediator that is in a reduced state (e.g., potassium ferrocyanide) is generated by the measurement of the amount of the blood cells. If the amount of the blood component and the amount of the interfering substance are measured thereafter, the reduced mediator thus generated causes a background noise, resulting in an error in the measured value.

(Step 5: Correcting Amount of Blood Component)

The amount of the glucose obtained in Step 2 is corrected using the amount of the interfering substance measured in Step 3 and the amount of the blood cells measured in Step 4. Preferably, the correction is carried out based on a calibration curve (including a calibration table) prepared previously. The corrected amount of the glucose is displayed on or stored in the measuring device.

Example 3

Figure 7:
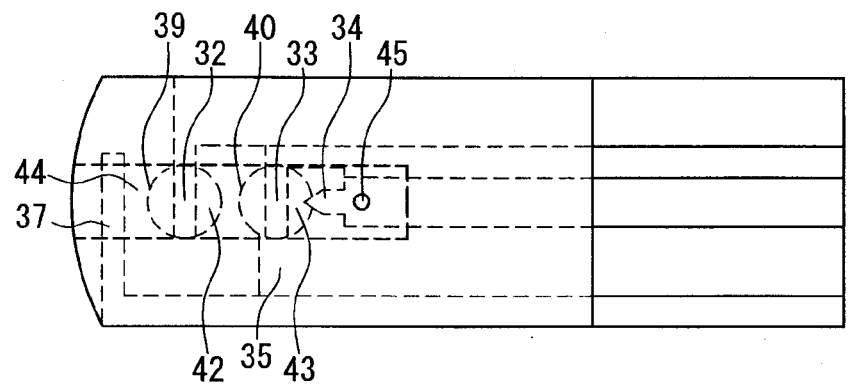
FIG. 7 is a plan view of still another example of a sensor according to the present invention.

FIG. 7 shows still another example of a sensor for measuring a blood component according to the present invention. FIG. 7 is a plan view showing an electrode pattern in this sensor, which corresponds to the electrode pattern shown in FIG. 6 in which either one or the combination of the electrodes of the first electrode system is shared with the third electrode system as the counter electrode. Except for the above, this sensor has the same configuration as the sensor according to Example 2, and the components, the configuration of the reagent layers, production method, etc. of this sensor are the same as those of the sensor according to Example 2.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1: Detecting Specimen (Blood))

The supply of blood to the sensor is detected by applying a voltage between the first counter electrode 35 and the liquid detecting electrode 34. It is to be noted here that the combination of the electrodes used for the blood supply detection is by no means limited to the above combination. After the supply of the blood has been confirmed, the subsequent step is started. The voltage applied in Step 1 is, for example, 0.05 to 1.0 V, preferably 0.1 to 0.8 V, and more preferably 0.2 to 0.5 V.

(Step 2: Measuring Glucose)

After allowing glucose in the blood to react with an oxidoreductase for a certain period of time, a voltage is applied to the first working electrode 33. In this step, the first working electrode 33 is used as a working electrode and the first counter electrode 35 is used as a counter electrode. A reduced mediator generated on the first working electrode 33 through the enzyme reaction is oxidized, and the oxidation current caused at this time is detected. The glucose is allowed to react with the oxidoreductase for, for example, 0 to 60 seconds, preferably 1 to 30 seconds, and more preferably 2 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Amount of Interfering Substance)

By applying a voltage to the third working electrode 32, a current caused by the electrolytic oxidation reaction of the interfering substance is detected. In this step, the third working electrode 32 is used as a working electrode and the first working electrode 33 is used as a counter electrode. The amount of the interfering substance is determined based on the result of this detection. The amount of the interfering substance is used for the correction in the measurement of the glucose. In this correction, the amount of the interfering substance determined using a previously prepared calibration curve showing the relationship between a current and an amount of the interfering substance may be used or alternatively the detected current may be used as it is. In Step 3, the voltage applied is, for example, 0.01 to 1 V and preferably 0.01 to 0.5 V, and the voltage application time is, for example, 0.001 to 60 seconds, preferably 0.01 to 10 seconds, and more preferably 0.01 to 5 seconds. Although the first working electrode 33 is used as the counter electrode in the present example, the present invention is not limited thereto. It should be noted that the first counter electrode 35 alone or the combination of the first working electrode 33 and the first counter electrode 35 also may be used as the counter electrode.

When the first working electrode 33 or the combination of the first working electrode 33 and the first counter electrode 35 is used as the counter electrode, Step 3 preferably is performed after the amount of the blood component has been measured. The reason why the amount of the interfering substance is measured after the amount of the blood component has been measured is as follows. When the amount of the interfering substance is measured before measuring the amount of the blood component, the following phenomenon occurs. That is, although the mediator that initially is in an oxidized state (e.g., potassium ferricyanide) is provided on the electrode(s) used as the counter electrode, the mediator that is in a reduced state (e.g., potassium ferrocyanide) is generated by the measurement of the amount of the interfering substance. If the reduced mediator thus generated diffuses on the first working electrode 33 for measuring the amount of the blood component, the mediator causes a background noise during the measurement of the amount of the blood component, resulting in an error in the measured value.

However, when the first counter electrode 35 alone is used as the counter electrode, Step 3 may be performed before measuring the amount of the blood component. The reason for this is that the amount of the mediator in a reduced state (e.g., potassium ferrocyanide) generated on the first counter electrode 35 is not large enough to diffuse on the first working electrode 33 and thus there is little chance that it might cause a background noise.

(Step 4: Measuring Amount of Blood Cells)

By applying a voltage to the second working electrode 37, an electrolytic current depending on the amount of the blood cells can be detected. In this step, the second working electrode 37 is used as a working electrode and the third working electrode 32 is used as a counter electrode. The amount of the blood cells is determined based on the result of this detection. The amount of the blood cells is used for the correction in the measurement of the glucose. In this correction, the amount of the blood cells determined using a previously prepared calibration curve showing the relationship between an electrolytic current and an amount of the blood cells may be used or alternatively the detected electrolytic current may be used as it is. In Step 4, the voltage applied is, for example, 1 to 10 V, preferably 1 to 5 V, and more preferably 2 to 3 V, and the voltage application time is, for example, 0.001 to 60 seconds, preferably 0.01 to 10 seconds, and more preferably 0.01 to 5 seconds. Preferably, Step 4 is performed as a last step in the series of steps. Although the third working electrode 32 is used as the counter electrode in the present example, the present invention is not limited thereto. It should be noted that the first working electrode 33 alone, the first counter electrode 35 alone, or the combination of the first working electrode 33 and the first counter electrode 35 also may be used as the counter electrode.

The reason why the measurement of the amount of the blood cells is performed last is the same as that described in Example 2.

(Step 5: Correcting Amount of Blood Component)

The amount of the glucose obtained in Step 2 is corrected using the amount of the interfering substance measured in Step 3 and the amount of the blood cells measured in Step 4. Preferably, the correction is carried out based on a calibration curve (including a calibration table) prepared previously. The corrected amount of the glucose is displayed on or stored in the measuring device.

Example 4

Figure 8:
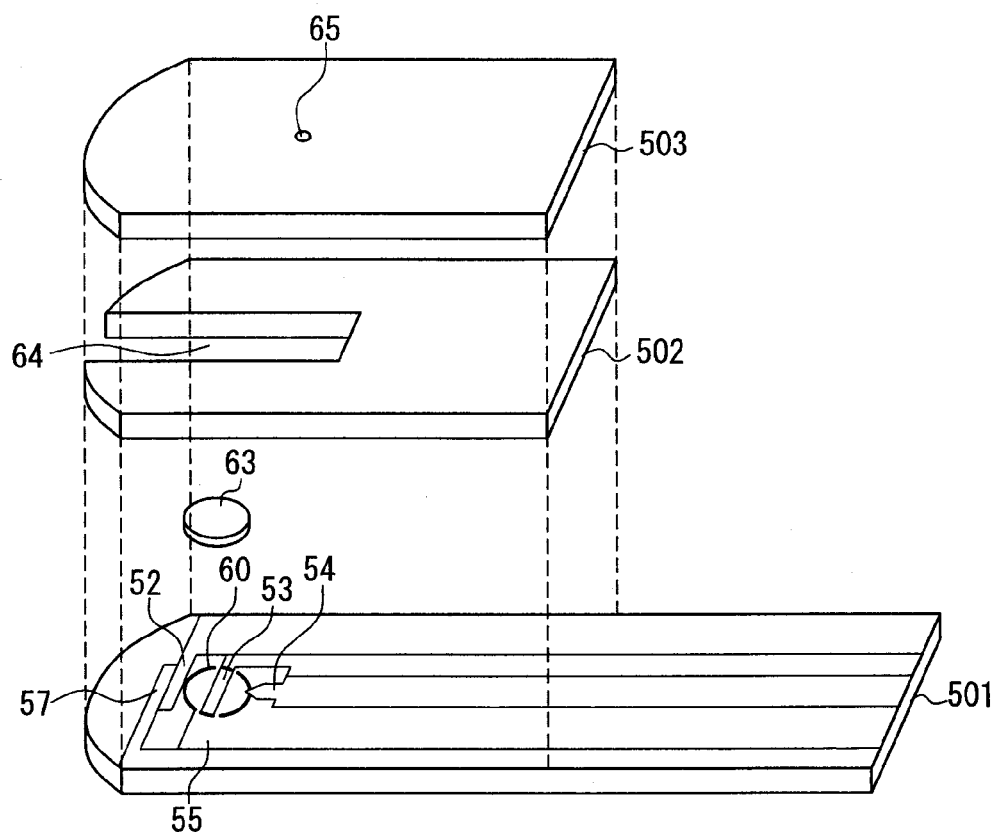
FIG. 8 is an exploded perspective view showing still another example of a sensor according to the present invention.
Figure 9:
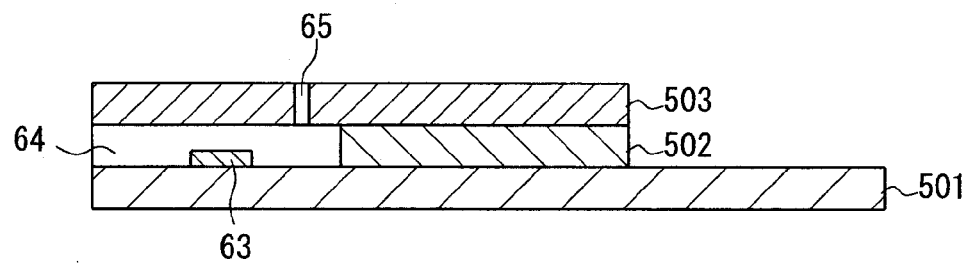
FIG. 9 is a sectional view of the sensor shown in FIG. 8.
Figure 10:
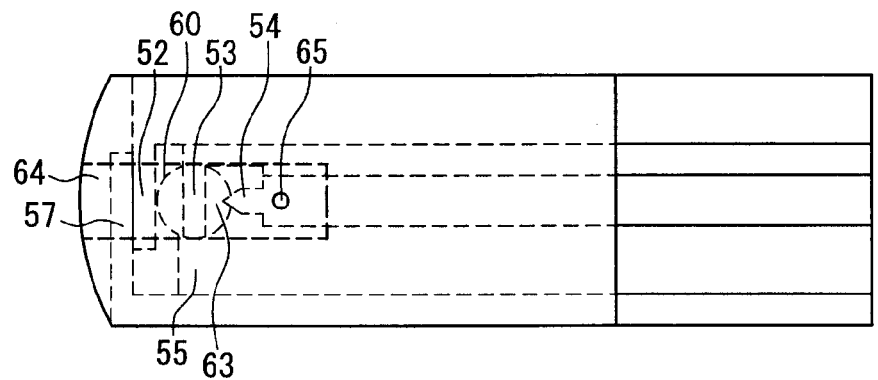
FIG. 10 is a plan view of the sensor shown in FIG. 8.

FIGS. 8, 9, and 10 show still another example of a sensor for measuring a blood component according to the present invention. FIG. 8 is an exploded perspective view of the sensor, FIG. 9 is a sectional view of the sensor, and FIG. 10 is a plan view of the sensor. In these three drawings, the same components are given the same reference numerals. The sensor according to the present example corresponds to the sensor according to Example 3 from which the third reagent layer provided on the third working electrode is removed. As shown in the drawings, in this sensor, a first electrode system including a first working electrode 53 and a first counter electrode 55, a second working electrode 57, a third working electrode 52, and a liquid detecting electrode 54 are formed on an insulating substrate 501. A first reagent layer 63 is provided on the first electrode system. The first reagent layer 63 contains an oxidoreductase such as glucose dehydrogenase and a mediator such as potassium ferricyanide and optionally contains an enzyme stabilizer, a crystal homogenizing agent, and the like. A cover 503 is disposed on the insulating substrate 501 so as to cover an entire area excluding one end portion (the end portion on the right in the drawings) with a spacer 502 intervening therebetween. In this sensor, the insulating substrate 501, the spacer 502, and the cover 503 form a channel 64 for leading blood to the respective electrodes (52 to 55, and 57). The channel 64 extends to the other end portion (the end portion on the left in the drawings) of the sensor, and the tip of the channel 64 is open toward the outside of the sensor so as to serve as a blood supply port. The five electrodes (52 to 55, and 57) are connected to leads, respectively. These leads extend to the above-described one end portion (the end portion on the right in the drawings) of the sensor with the tip of each lead not being covered with the cover but being exposed. The cover 503 has an air hole 65 at a portion corresponding to the right end portion of the channel 64.

The first reagent layer 63 is formed in the following manner. For example, an aqueous solution containing 0.1 to 5 U/sensor of glucose dehydrogenase, 10 to 200 mM of potassium ferricyanide, 1 to 50 mM of maltitol, and 20 to 200 mM of taurine is dropped on a round slit portion 60 and then is dried. By providing this slit portion 60, it becomes possible to suppress the spreading of the droplet of the aqueous solution, thereby allowing the first reagent layer 63 to be provided at a desired position more accurately. In this manner, the first reagent layer 63 is formed on the first working electrode 53 and the first counter electrode 55. The drying may be natural drying or forced drying using warm air, for example. However, if the temperature of the warm air is too high, there is a possibility that the enzyme contained in the solution might be deactivated. Thus, the temperature of the warm air preferably is around 50° C.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1: Detecting Specimen (Blood))

The supply of blood to the sensor is detected by applying a voltage between the first counter electrode 55 and the liquid detecting electrode 54. It is to be noted here that the combination of the electrodes used for the blood supply detection is by no means limited to the above combination. After the supply of the blood has been confirmed, the subsequent step is started. The voltage applied in Step 1 is, for example, 0.05 to 1.0 V, preferably 0.1 to 0.8 V, and more preferably 0.2 to 0.5 V.

(Step 2: Measuring Glucose)

After allowing glucose in the blood to react with an oxidoreductase for a certain period of time, a voltage is applied to the first working electrode 53. In this step, the first working electrode 53 is used as a working electrode and the first counter electrode 55 is used as a counter electrode. A reduced mediator generated on the first working electrode 53 through the enzyme reaction is oxidized, and the oxidation current caused at this time is detected. The glucose is allowed to react with the oxidoreductase for, for example, 0 to 60 seconds, preferably 1 to 30 seconds, and more preferably 2 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Amount of Interfering Substance)

By applying a voltage to the third working electrode 52, a current caused by the electrolytic oxidation reaction of the interfering substance is detected. In this step, the third working electrode 52 is used as a working electrode and the first working electrode 53 is used as a counter electrode. The amount of the interfering substance is determined based on the result of this detection. The amount of the interfering substance is used for the correction in the measurement of the glucose. In this correction, the amount of the interfering substance determined using a previously prepared calibration curve showing the relationship between a current and an amount of the interfering substance may be used or alternatively the detected current may be used as it is. In Step 3, the voltage applied is, for example, 0.01 to 1 V and preferably 0.01 to 0.5 V, and the voltage application time is, for example, 0.001 to 60 seconds, preferably 0.01 to 10 seconds, and more preferably 0.01 to 5 seconds. Although the first working electrode 53 is used as the counter electrode in the present example, the present invention is not limited thereto. It should be noted that the first counter electrode 55 alone or the combination of the first working electrode 53 and the first counter electrode 55 also may be used as the counter electrode.

When the first working electrode 53 or the combination of the first working electrode 53 and the first counter electrode 55 is used as the counter electrode, Step 3 preferably is performed after the amount of the blood component has been measured. The reason why the amount of the interfering substance is measured after the amount of the blood component has been measured is the same as that described in Example 3.

(Step 4: Measuring Amount of Blood Cells)

By applying a voltage to the second working electrode 57, an electrolytic current depending on the amount of the blood cells can be detected. In this step, the second working electrode 57 is used as a working electrode and the first working electrode 53 is used as a counter electrode. The amount of the blood cells is determined based on the result of this detection. The reason why the first working electrode 53 is used as the counter electrode is as follows. After the amount of the blood component has been measured, the mediator that is in an oxidized state (e.g., potassium ferricyanide) is present dominantly on the first working electrode 53. Thus, when the first working electrode 53 is used as the counter electrode for measuring the amount of the blood cells, it is possible to suppress the electrolytic reduction reaction occurring at the counter electrode from being a rate-determining step. The amount of the blood cells is used for the correction in the measurement of the glucose. In this correction, the amount of the blood cells determined using a previously prepared calibration curve showing the relationship between an electrolytic current and an amount of the blood cells may be used or alternatively the detected electrolytic current may be used as it is. In Step 4, the voltage applied is, for example, 1 to 10 V, preferably 1 to 5 V, and more preferably 2 to 3 V, and the voltage application time is, for example, 0.001 to 60 seconds, preferably 0.01 to 10 seconds, and more preferably 0.01 to 5 seconds. Preferably, Step 4 is performed as a last step in the series of steps. Although the first working electrode 53 is used as the counter electrode in the present example, the present invention is not limited thereto. It should be noted that the first counter electrode 55 alone or the combination of the first working electrode 53 and the first counter electrode 55 also may be used as the counter electrode.

The reason why the measurement of the amount of the blood cells is performed last is the same as that described in Example 2.

(Step 5: Correcting Amount of Blood Component)

The amount of the glucose obtained in Step 2 is corrected using the amount of the interfering substance measured in Step 3 and the amount of the blood cells measured in Step 4. Preferably, the correction is carried out based on a calibration curve (including a calibration table) prepared previously. The corrected amount of the glucose is displayed on or stored in the measuring device.

Example 5

Figure 11:
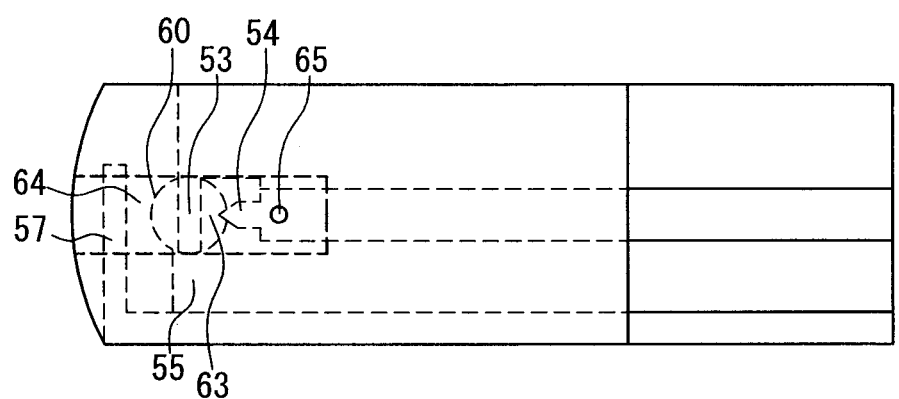
FIG. 11 is a plan view of still another example of a sensor according to the present invention.

FIG. 11 shows still another example of a sensor for measuring a blood component according to the present invention. FIG. 11 is a plan view showing an electrode pattern in this sensor, which corresponds to the electrode pattern shown in FIG. 10 in which the second working electrode serves also as the third working electrode. Except for the above, this sensor has the same configuration as the sensor according to Example 4, and the components, the configuration of the reagent layers, production method, etc. of this sensor are the same as those of the sensor according to Example 4.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1: Detecting Specimen (Blood))

The supply of blood to the sensor is detected by applying a voltage between the first counter electrode 55 and the liquid detecting electrode 54. It is to be noted here that the combination of the electrodes used for the blood supply detection is by no means limited to the above combination. After the supply of the blood has been confirmed, the subsequent step is started. The voltage applied in Step 1 is, for example, 0.05 to 1.0 V, preferably 0.1 to 0.8 V, and more preferably 0.2 to 0.5 V.

(Step 2: Measuring Glucose)

After allowing glucose in the blood to react with an oxidoreductase for a certain period of time, a voltage is applied to the first working electrode 53. In this step, the first working electrode 53 is used as a working electrode and the first counter electrode 55 is used as a counter electrode. A reduced mediator generated on the first working electrode 53 through the enzyme reaction is oxidized, and the oxidation current caused at this time is detected. The glucose is allowed to react with the oxidoreductase for, for example, 0 to 60 seconds, preferably 1 to 30 seconds, and more preferably 2 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Amount of Interfering Substance)

By applying a voltage to the second working electrode 57, a current caused by the electrolytic oxidation reaction of the interfering substance is detected. In this step, the second working electrode 57 is used as a working electrode and the first working electrode 53 is used as a counter electrode. The amount of the interfering substance is determined based on the result of this detection. The amount of the interfering substance is used for the correction in the measurement of the glucose. In this correction, the amount of the interfering substance determined using a previously prepared calibration curve showing the relationship between a current and an amount of the interfering substance may be used or alternatively the detected current may be used as it is. In Step 3, the voltage applied is, for example, 0.01 to 1 V and preferably 0.01 to 0.5 V, and the voltage application time is, for example, 0.001 to 60 seconds, preferably 0.01 to 10 seconds, and more preferably 0.01 to 5 seconds. Although the first working electrode 53 is used as the counter electrode in the present example, the present invention is not limited thereto. It should be noted that the first counter electrode 55 alone or the combination of the first working electrode 53 and the first counter electrode 55 also may be used as the counter electrode.

When the first working electrode 53 or the combination of the first working electrode 53 and the first counter electrode 55 is used as the counter electrode, Step 3 preferably is performed after the amount of the blood component has been measured. The reason why the amount of the interfering substance is measured after the amount of the blood component has been measured is the same as that described in Example 3.

(Step 4: Measuring Amount of Blood Cells)

By applying a voltage to the second working electrode 57, an electrolytic current depending on the amount of the blood cells can be detected. In this step, the second working electrode 57 is used as a working electrode and the first working electrode 53 is used as a counter electrode. The amount of the blood cells is determined based on the result of this detection. The reason why the first working electrode 53 is used as the counter electrode is the same as that described in Example 4. The amount of the blood cells is used for the correction in the measurement of the glucose. In this correction, the amount of the blood cells determined using a previously prepared calibration curve showing the relationship between an electrolytic current and an amount of the blood cells may be used or alternatively the detected electrolytic current may be used as it is. In Step 4, the voltage applied is, for example, 1 to 10 V, preferably 1 to 5 V, and more preferably 2 to 3 V, and the voltage application time is, for example, 0.001 to 60 seconds, preferably 0.01 to 10 seconds, and more preferably 0.01 to 5 seconds. Preferably, Step 4 is performed as a last step in the series of steps. Although the first working electrode 53 is used as the counter electrode in the present example, the present invention is not limited thereto. It should be noted that the first counter electrode 55 alone or the combination of the first working electrode 53 and the first counter electrode 55 also may be used as the counter electrode.

The reason why the measurement of the amount of the blood cells is performed last is the same as that described in Example 2.

(Step 5: Correcting Amount of Blood Component)

The amount of the glucose obtained in Step 2 is corrected using the amount of the interfering substance measured in Step 3 and the amount of the blood cells measured in Step 4. Preferably, the correction is carried out based on a calibration curve (including a calibration table) prepared previously. The corrected amount of the glucose is displayed on or stored in the measuring device.

Example 6

Example 6 is directed to an example where a sensor as shown in FIG. 11 was used as in Example 5 and an electrode pretreatment further is performed.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1: Detecting Specimen (Blood))

The supply of blood to the sensor is detected by applying a voltage between the first counter electrode 55 and the liquid detecting electrode 54. It is to be noted here that the combination of the electrodes used for the blood supply detection is by no means limited to the above combination. After the supply of the blood has been confirmed, the subsequent step is started. The voltage applied in Step 1 is, for example, 0.05 to 1.0 V, preferably 0.1 to 0.8 V, and more preferably 0.2 to 0.5 V.

(Step 2: Pretreating Electrode)

A voltage is applied to the second working electrode 57 to clean the surface of the second working electrode 57. In this step, the second working electrode 57 is used as a working electrode and the first counter electrode 55 is used as a counter electrode. In Step 2, the voltage applied preferably is in the range from 0.01 to 1 V and more preferably from 0.01 to 0.5 V, and the voltage application time is, for example, 0.001 to 30 seconds, preferably 0.01 to 10 seconds, and more preferably 0.01 to 5 seconds. By performing this pretreatment, the surface of the second working electrode 57 is cleaned, so that the amount of the interfering substance can be measured more accurately. Step 2 may be performed simultaneously with or after Step 4 (the measurement of glucose) to be described later.

As long as Step 2 is performed before measuring the amount of the interfering substance and the amount of the blood cells, Step 2 can be performed at the most effective timing from the viewpoint of simplicity in operation and reduction in time required for the whole measurement process.

(Step 3: Measuring Amount of Interfering Substance)

By applying a voltage to the second working electrode 57, a current caused by the electrolytic oxidation reaction of the interfering substance is detected. In this step, the second working electrode 57 is used as a working electrode and the first counter electrode 55 is used as a counter electrode. The amount of the interfering substance is determined based on the result of this detection. The amount of the interfering substance is used for the correction in the measurement of the glucose. In this correction, the amount of the interfering substance determined using a previously prepared calibration curve showing the relationship between a current and an amount of the interfering substance may be used or alternatively the detected current may be used as it is. In Step 3, the voltage applied is, for example, 0.01 to 1 V and preferably 0.01 to 0.5 V, and the voltage application time is, for example, 0.001 to 60 seconds, preferably 0.01 to 10 seconds, and more preferably 0.01 to 5 seconds. Although the first counter electrode 55 is used as the counter electrode in the present example, the present invention is not limited thereto. It should be noted that the first working electrode 53 alone or the combination of the first working electrode 53 and the first counter electrode 55 also may be used as the counter electrode.

When the first working electrode 53 or the combination of the first working electrode 53 and the first counter electrode 55 is used as the counter electrode, Step 3 preferably is performed after the amount of the blood component has been measured. The reason why the amount of the interfering substance is measured after the amount of the blood component has been measured is the same as that described in Example 3. However, when the first counter electrode 55 alone is used as the counter electrode as in the present Example 6, Step 3 may be performed before measuring the amount of the blood component. The reason for this is that, in this case, the amount of the mediator in a reduced state (e.g., potassium ferrocyanide) generated on the first counter electrode 55 is not large enough to diffuse on the first working electrode 33 and thus there is little chance that it might cause a background noise.

(Step 4: Measuring Glucose)

After allowing glucose in the blood to react with an oxidoreductase for a certain period of time, a voltage is applied to the first working electrode 53. In this step, the first working electrode 53 is used as a working electrode and the first counter electrode 55 is used as a counter electrode. A reduced mediator generated on the first working electrode 53 through the enzyme reaction is oxidized, and the oxidation current caused at this time is detected. The glucose is allowed to react with the oxidoreductase for, for example, 0 to 60 seconds, preferably 1 to 30 seconds, and more preferably 2 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 5: Measuring Amount of Blood Cells)

By applying a voltage to the second working electrode 57, an electrolytic current depending on the amount of the blood cells can be detected. In this step, the second working electrode 57 is used as a working electrode and the first working electrode 53 is used as a counter electrode. The amount of the blood cells is determined based on the result of this detection. The amount of the blood cells is used for the correction in the measurement of the glucose. In this correction, the amount of the blood cells determined using a previously prepared calibration curve showing the relationship between an electrolytic current and an amount of the blood cells may be used or alternatively the detected electrolytic current may be used as it is. In Step 4, the voltage applied is, for example, 1 to 10 V, preferably 1 to 5 V, and more preferably 2 to 3 V, and the voltage application time is, for example, 0.001 to 60 seconds, preferably 0.01 to 10 seconds, and more preferably 0.01 to 5 seconds. Preferably, Step 4 is performed as a last step in the series of steps. Although the first working electrode 53 is used as the counter electrode in the present example, the present invention is not limited thereto. It should be noted that the first counter electrode 55 alone or the combination of the first working electrode 53 and the first counter electrode 55 also may be used as the counter electrode.

The reason why the measurement of the amount of the blood cells is performed last is the same as that described in Example 2.

(Step 6: Correcting Amount of Blood Component)

The amount of the glucose obtained in Step 4 is corrected using the amount of the interfering substance measured in Step 3 and the amount of the blood cells measured in Step 5. Preferably, the correction is carried out based on a calibration curve (including a calibration table) prepared previously. The corrected amount of the glucose is displayed on or stored in the measuring device.

As an example of the blood component measurement, Examples 1 to 6 describe the case where the glucose concentration in blood is measured. However, the present invention is by no means limited thereto. As already described above, the present invention also is useful for the measurement of other blood components, such as lactic acid and cholesterol.

Although several electrode patterns are shown in Examples 1 to 6, the present invention is by no means limited thereto. It is to be noted here that the electrode pattern can be changed as appropriate depending on the purpose or the conditions of use of the sensor, for example.

Reference Example 1

A sensor having a configuration shown in FIGS. 1, 2, and 3 was produced. The first reagent layer 23 was formed by dissolving glucose dehydrogenase (1 to 5 U), potassium ferricyanide (60 mM), and taurine (80 mM) in a CMC aqueous solution (0.1 wt %) to prepare a reagent solution, dropping the reagent solution on the round slit portion 20, and then drying it. The second reagent layer 21 and the third reagent layer 22 were formed by dissolving potassium ferricyanide (60 mM) and taurine (80 mM) in a CMC aqueous solution (0.1 wt %) to prepare a reagent solution, dropping the reagent solution on the round slit portions 18 and 19, and then drying it.

Using this sensor, a response current for determining the amount of an interfering substance was measured. Ascorbic acid was used as an example of an easily oxidizable interfering substance, and blood samples respectively containing 0, 5, 10, and 20 mg/dl of ascorbic acid were provided. Using the thus-prepared four blood samples, a current flowing through the third electrode system was measured. The measurement was performed by applying a voltage of 0.5 V to the third working electrode 12 for 3 seconds.

Next, using the same sensor, a response current for determining the amount of blood cells was measured. Three types of blood samples in which the amounts of blood cells were adjusted to be 25%, 45%, and 65%, respectively, were provided. Using the thus-prepared three blood samples, an electrolytic current flowing through the second electrode system was measured. Using the third working electrode 32 as a counter electrode, the measurement was performed by applying a voltage of 2.5 V to the second working electrode 17 for 3 seconds.

Reference Example 2

A sensor having a configuration shown in FIGS. 4, 5, and 6 was produced. The first reagent layer 43 was formed by dissolving glucose dehydrogenase (1 to 5 U), potassium ferricyanide (60 mM), and taurine (80 mM) in a CMC aqueous solution (0.1 wt %) to prepare a reagent solution, dropping the reagent solution on the round slit portion 40, and then drying it. The third reagent layer 42 was formed by dissolving potassium ferricyanide (60 mM) and taurine (80 mM) in a CMC aqueous solution (0.1 wt %) to prepare a reagent solution, dropping the reagent solution on the round slit portion 39, and then drying it.

Using this sensor, a response current for determining the amount of an interfering substance was measured. Ascorbic acid was used as an example of an easily oxidizable interfering substance, and blood samples respectively containing 0, 5, 10, and 20 mg/dl of ascorbic acid were provided. Using the thus-prepared four blood samples, a current flowing through the third electrode system was measured. The measurement was performed by applying a voltage of 0.5 V to the third working electrode 32 for 3 seconds.

Next, using the same sensor, a response current for determining the amount of blood cells was measured. Three types of blood samples in which the amounts of blood cells were adjusted to be 25%, 45%, and 65%, respectively, were provided. Using the thus-prepared three blood samples, an electrolytic current flowing through the second electrode system was measured. The measurement was performed by applying a voltage of 2.5 V to the second working electrode 37 for 3 seconds.

Reference Example 3

A sensor having a configuration shown in FIG. 7 was produced. The first reagent layer 43 was formed by dissolving glucose dehydrogenase (1 to 5 U), potassium ferricyanide (60 mM), and taurine (80 mM) in a CMC aqueous solution (0.1 wt %) to prepare a reagent solution, dropping the reagent solution on the round slit portion 40, and then drying it. The third reagent layer 42 was formed by dissolving potassium ferricyanide (60 mM) and taurine (80 mM) in a CMC aqueous solution (0.1 wt %) to prepare a reagent solution, dropping the reagent solution on the round slit portion 39, and then drying it.

Using this sensor, a response current for determining the amount of an interfering substance was measured. Ascorbic acid was used as an example of an easily oxidizable interfering substance, and blood samples respectively containing 0, 5, 10, and 20 mg/dl of ascorbic acid were provided. Using the thus-prepared four blood samples, a current flowing through the third electrode system was measured. Using the first working electrode 33 as a counter electrode, the measurement was performed by applying a voltage of 0.5 V to the third working electrode 32 for 3 seconds.

Next, using the same sensor, a response current for determining the amount of blood cells was measured. Three types of blood samples in which the amounts of blood cells were adjusted to be 25%, 45%, and 65%, respectively, were provided. Using the thus-prepared three blood samples, an electrolytic current flowing through the second electrode system was measured. Using the third working electrode 32 as a counter electrode, the measurement was performed by applying a voltage of 2.5 V to the second working electrode 37 for 3 seconds.

Reference Example 4

A sensor having a configuration shown in FIGS. 8, 9, and 10 was produced. The first reagent layer 63 was formed by dissolving glucose dehydrogenase (1 to 5 U), potassium ferricyanide (60 mM), and taurine (80 mM) in a CMC aqueous solution (0.1 wt %) to prepare a reagent solution, dropping the reagent solution on the round slit portion 60, and then drying it.

Using this sensor, a response current for determining the amount of an interfering substance was measured. Ascorbic acid was used as an example of an easily oxidizable interfering substance, and blood samples respectively containing 0, 5, 10, and 20 mg/dl of ascorbic acid were provided. Using the thus-prepared four blood samples, a current flowing through the third electrode system was measured. Using the first working electrode 53 as a counter electrode, the measurement was performed by applying a voltage of 0.5 V to the third working electrode 52 for 3 seconds.

Next, using the same sensor, a response current for determining the amount of blood cells was measured. Three types of blood samples in which the amounts of blood cells were adjusted to be 25%, 45%, and 65%, respectively, were provided. Using the thus-prepared three blood samples, an electrolytic current flowing through the second electrode system was measured. Using the first working electrode 53 as a counter electrode, the measurement was performed by applying a voltage of 2.5 V to the second working electrode 57 for 3 seconds.

Reference Example 5

A sensor having a configuration shown in FIG. 11 was produced. The first reagent layer 63 was formed by dissolving glucose dehydrogenase (1 to 5 U), potassium ferricyanide (60 mM), and taurine (80 mM) in a CMC aqueous solution (0.1 wt %) to prepare a reagent solution, dropping the reagent solution on the round slit portion 60, and then drying it.

Using this sensor, a response current for determining the amount of an interfering substance was measured. Ascorbic acid was used as an example of an easily oxidizable interfering substance, and blood samples respectively containing 0, 5, 10, and 20 mg/dl of ascorbic acid were provided. Using the thus-prepared four blood samples, a current flowing through the third electrode system was measured. Using the first working electrode 53 as a counter electrode, the measurement was performed by applying a voltage of 0.5 V to the third working electrode 52 for 3 seconds.

Next, using the same sensor, a response current for determining the amount of blood cells was measured. Three types of blood samples in which the amounts of blood cells were adjusted to be 25%, 45%, and 65%, respectively, were provided. Using the thus-prepared three blood samples, an electrolytic current flowing through the second electrode system was measured. Using the first working electrode 53 as a counter electrode, the measurement was performed by applying a voltage of 2.5 V to the second working electrode 57 for 3 seconds.

Figure 12:
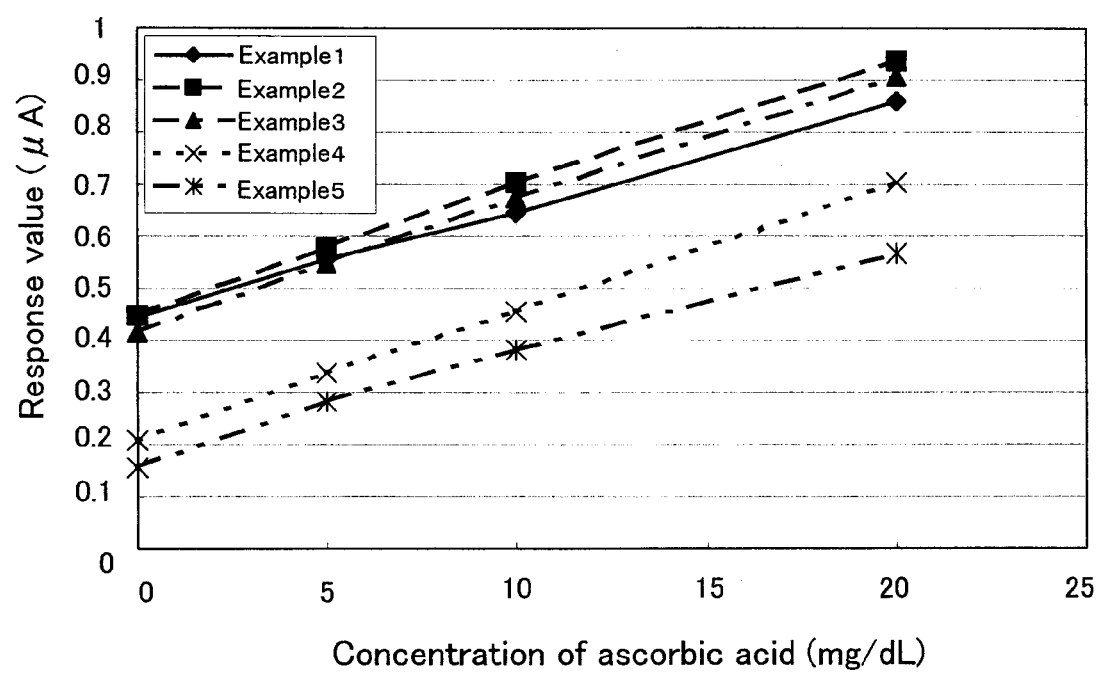
FIG. 12 is a graph showing an example of the result of measurement of a response current for determining the amount of an interfering substance.
Figure 13A:
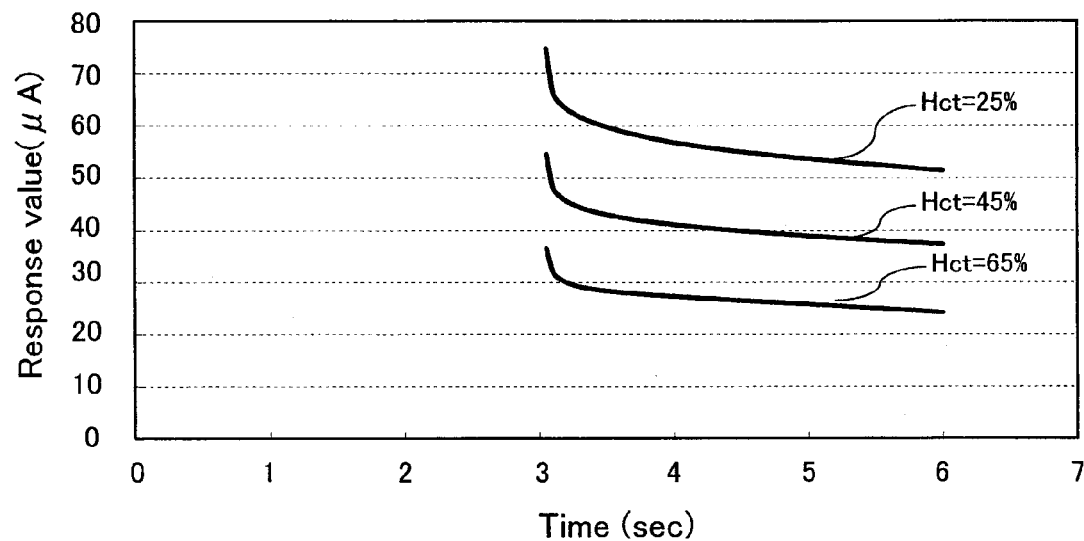
FIG. 13A is a graph showing changes in response current ($\mu A$) over time during application of a voltage (V)
Figure 13B:
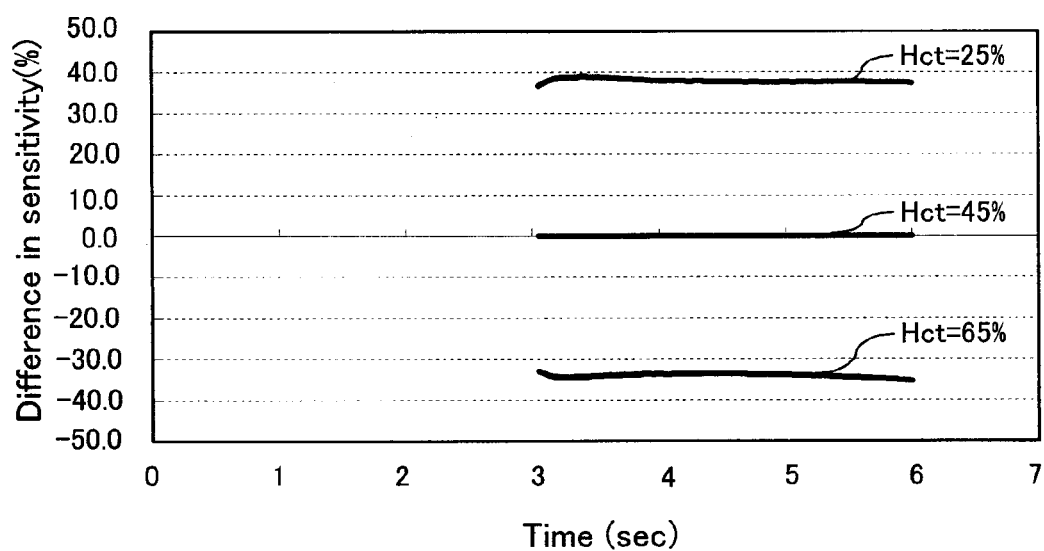
FIG. 13B is a graph showing changes in difference in sensitivity (%) over time during the application of the voltage (V).
Figure 14A:
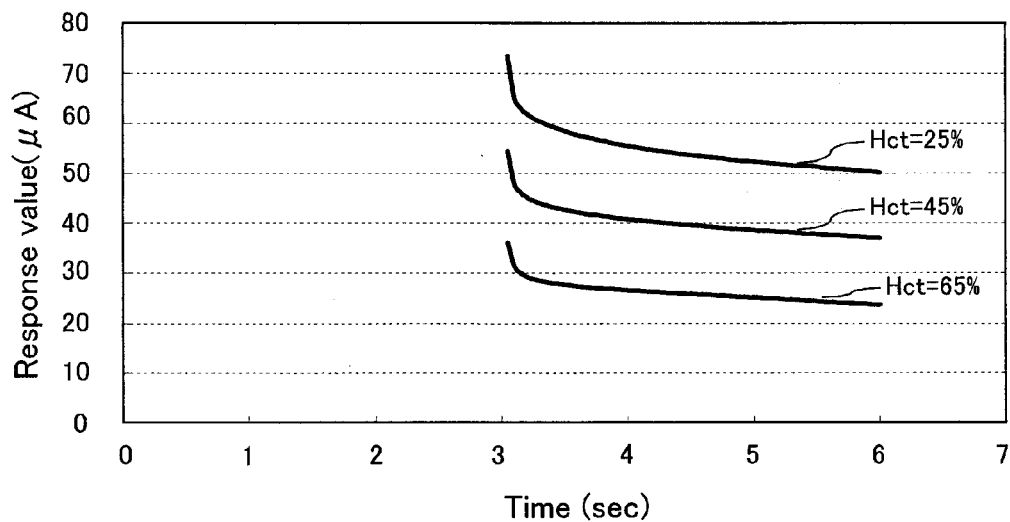
FIG. 14A is a graph showing changes in response current ($\mu A$) over time during application of a voltage (V)
Figure 14B:
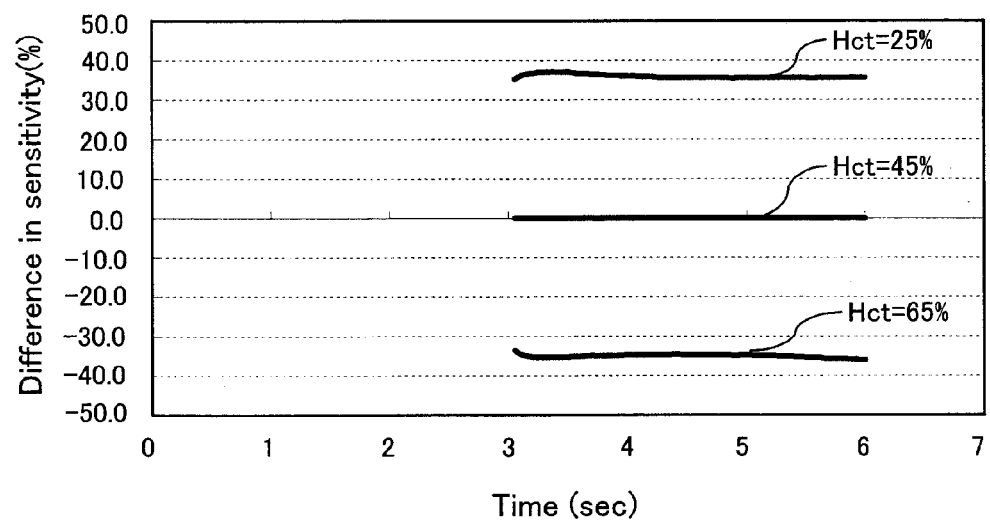
FIG. 14B is a graph showing changes in difference in sensitivity (%) over time during the application of the voltage (V).
Figure 15A:
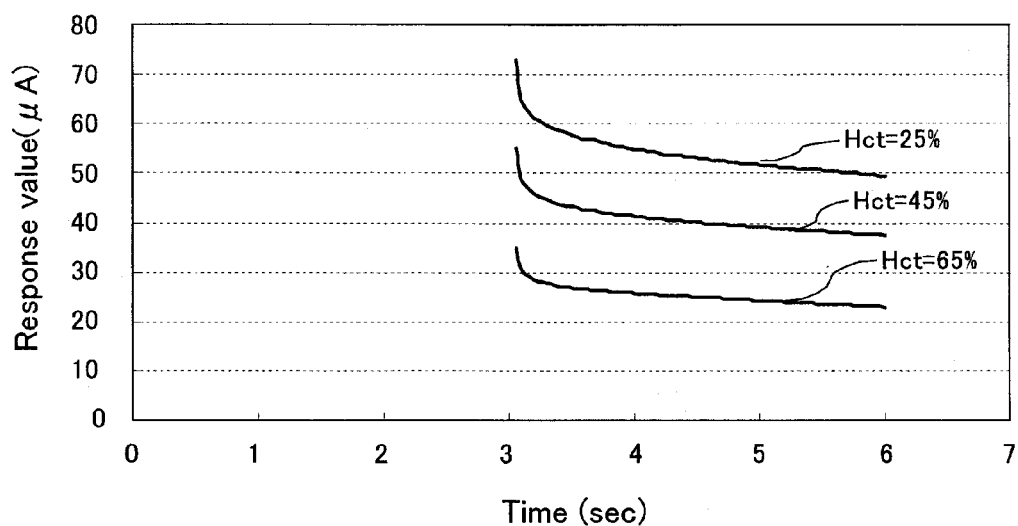
FIG. 15A is a graph showing changes in response current ($\mu A$) over time during application of a voltage (V)
Figure 15B:
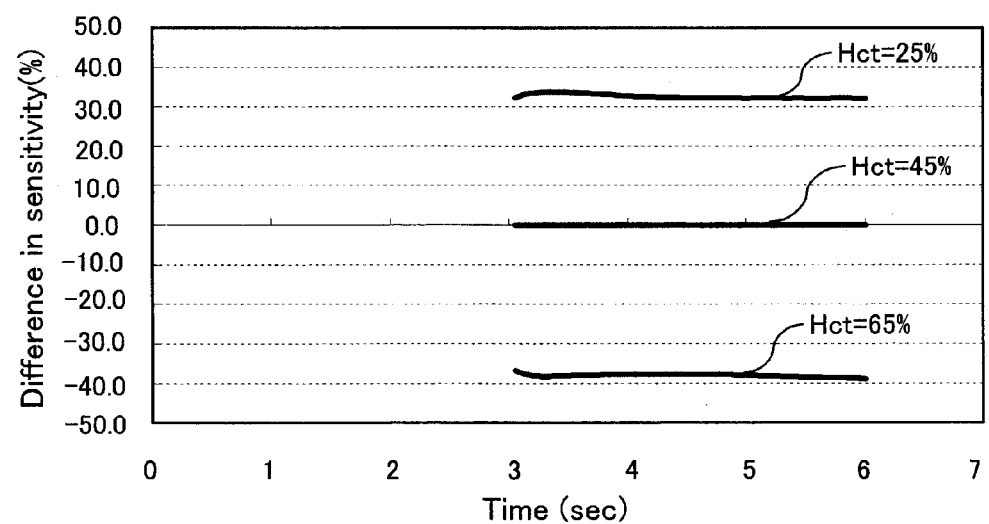
FIG. 15B is a graph showing changes in difference in sensitivity (%) over time during the application of the voltage (V).
Figure 16A:
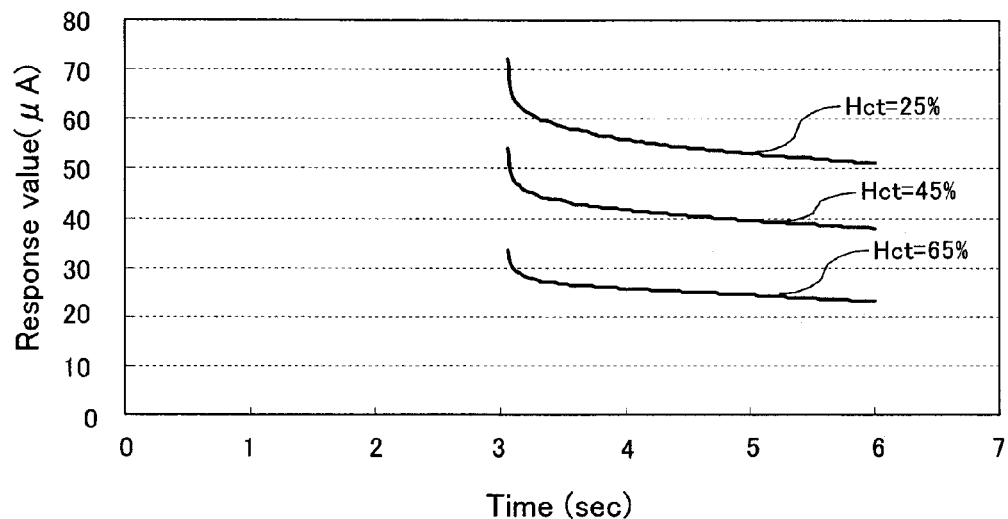
FIG. 16A is a graph showing changes in response current ($\mu A$) over time during application of a voltage (V)
Figure 16B:
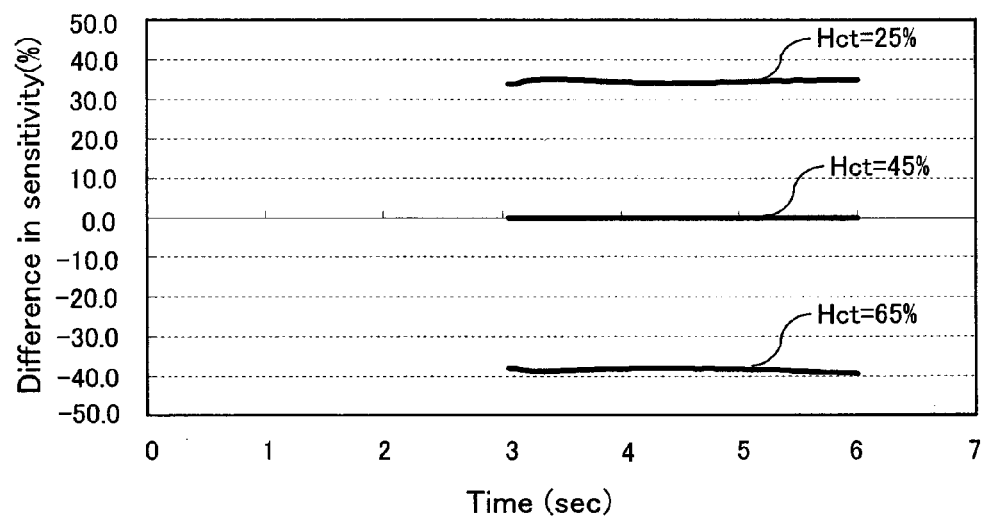
FIG. 16B is a graph showing changes in difference in sensitivity (%) over time during the application of the voltage (V).
Figure 17A:
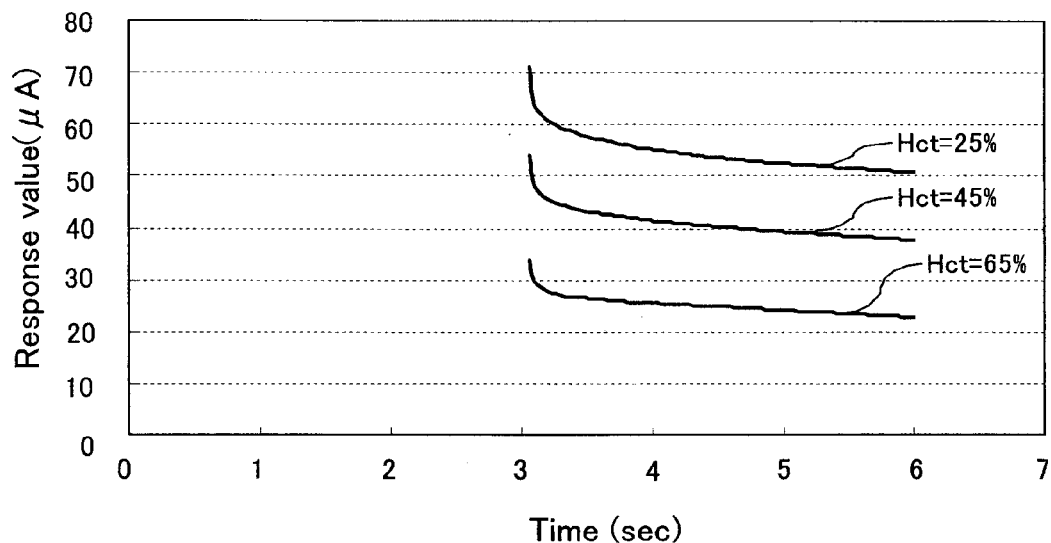
FIG. 17A is a graph showing changes in response current ($\mu A$) over time during application of a voltage (V)
Figure 17B:
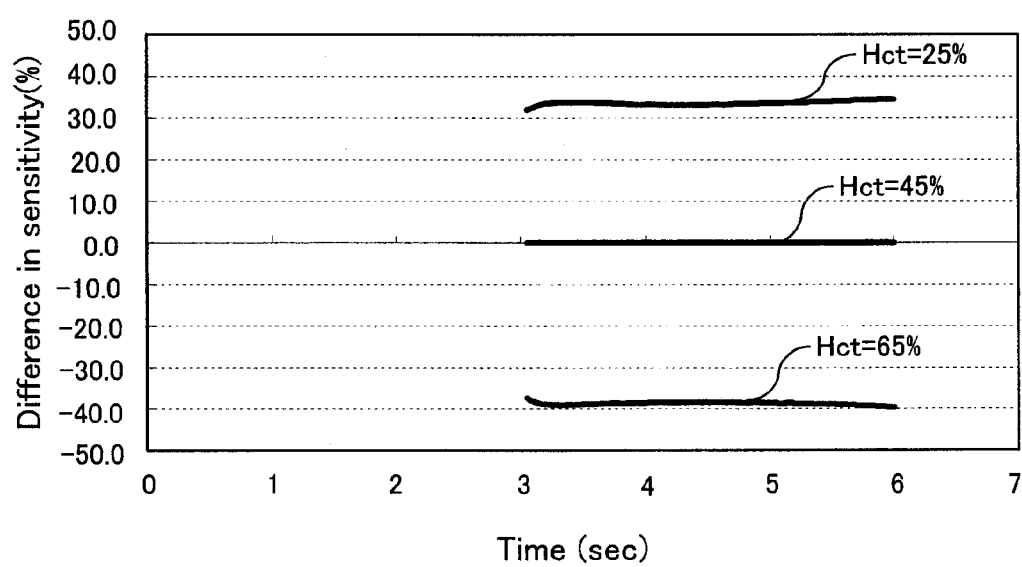
FIG. 17B is a graph showing changes in difference in sensitivity (%) over time during the application of the voltage (V).

FIG. 12 is a graph showing the result of measurements of the response currents for determining the amount of the interfering substance in Reference Examples 1 to 5. As can be seen from FIG. 12, the response currents reflecting the amounts of the interfering substance could be detected.

FIGS. 13 to 17 show the result of measurements of the response currents for determining the amount of the blood cells in Reference Examples 1 to 5. In FIGS. 13 to 17, FIGS. 13A to 17A are graphs each showing changes in response current ($\mu$A) over time during the application of the voltage (V), and FIGS. 13B to 17B are graphs each showing changes in difference in sensitivity (%) over time during the application of the voltage (V). As can be seen from these drawings, according to the sensors of Reference Examples 1 to 5, the difference in sensitivity did not depend on the voltage application time, so that the response current reflecting the amount of the blood cells could be detected definitely.

INDUSTRIAL APPLICABILITY

The method of measuring a blood component according to the present invention measures the amounts of an interfering substance and blood cells with high accuracy and high reliability and corrects the amount of the blood component based on the amounts of the interfering substance and the blood cells. Thus, the method of the present invention can measure the blood component with high accuracy and high reliability. Accordingly, the present invention is useful for the measurement of a blood component such as glucose.

The invention claimed is:
1. A biosensor for measuring a component in blood, wherein the biosensor comprises:
   a first analysis portion comprising a first electrode system on which at least an oxidoreductase that acts upon the component and a mediator are provided, the first electrode system comprising a working electrode and a counter electrode;
   a second analysis portion comprising a second electrode system that comprises a working electrode and a counter electrode, a mediator being provided on the counter electrode but not on the working electrode; and
   a third analysis portion comprising a third electrode system that comprises a working electrode and a counter electrode, in the first analysis portion, the component in the blood is measured by causing a redox reaction between the component and the oxidoreductase in the presence of the mediator and detecting with the first electrode system a redox current caused to flow when a voltage is applied, in the second analysis portion, an amount of blood cells contained in the blood is measured by supplying the blood to the second electrode system, applying a voltage to the second electrode system in this state to cause a redox current to flow through the second electrode system, and detecting the redox current, in the third analysis portion, an amount of an interfering substance contained in the blood is measured by supplying the blood to the third electrode system, applying a voltage to the third electrode system in this state to cause a redox current to flow through the third electrode system, and detecting the redox current, and the working electrodes and the counter electrodes of the first, second and third electrode systems are made of gold, platinum, or palladium.

2. The biosensor according to claim 1, wherein, in the third electrode system, a mediator is provided at least on the counter electrode.

3. The biosensor according to claim 1, further comprising a channel for leading blood to the biosensor, wherein the working electrode of the second analysis portion is located furthest upstream, and the first electrode system, the counter electrode of the second system and the third electrode system are located downstream with respect to flow of the blood supplied from a first end of the channel, or the working electrode of the third analysis portion is located furthest upstream and the first electrode system, and the second system and the counter electrode of the third electrode system are located downstream with respect to flow of the blood supplied from one end of the channel.

4. The biosensor according to claim 3, wherein the first analysis portion is located furthest downstream in the channel.

5. The biosensor according to claim 1, wherein at least one electrode selected from the working electrodes and the counter electrodes of the first electrode system, the second electrode system, and the third electrode system serves also as any of the other electrodes.

6. The biosensor according to claim 5, wherein a mediator is not provided on the working electrode of the third electrode system, and the working electrode of the second electrode serves also as the working electrode of the third electrode.

7. The biosensor according to claim 6, wherein either one or a combination of the electrodes of the first electrode system serves also as at least one of the second electrode system and the third electrode system as the counter electrode.

8. The biosensor according to claim 5, wherein the counter electrode of the second electrode system serves also as the working electrode of the third electrode system.

9. The biosensor according to claim 5, wherein the counter electrode of the second electrode system serves also as the working electrode of the third electrode system and the counter electrode of the third electrode system serves also as the counter electrode of the first electrode system.

10. The biosensor according to claim 1, further comprising a liquid detecting electrode, wherein the liquid detecting electrode is located downstream from at least one of the analysis portions so that whether or not the blood is supplied to the at least one of the analysis portions can be detected with the liquid detecting electrode.

* * * * *